US012727911B2

(12) United States Patent
Solem et al.

(10) Patent No.: US 12,727,911 B2
(45) Date of Patent: Sep. 8, 2026

(54) INTERFACE FOR ACCESSING THE INTERIOR OF A HEART

(71) Applicant: Syntach AG, Schaffhausen (CH)

(72) Inventors: Jan Otto Solem, Schaffhausen (CH); Kristian Solem, Schaffhausen (CH); Daniel Engvall, Schaffhausen (CH); Martin Wolff, Schaffhausen (CH)

(73) Assignee: Syntach AG, Schaffhausen (CH)

(*) Notice: Subject to any disclaimer, the term of this patent is extended or adjusted under 35 U.S.C. 154(b) by 517 days.

(21) Appl. No.: 17/805,649

(22) Filed: Jun. 6, 2022

(65) Prior Publication Data

US 2022/0323105 A1 Oct. 13, 2022

Related U.S. Application Data

(63) Continuation of application No. PCT/EP2020/088064, filed on Dec. 30, 2020, which (Continued)

(51) Int. Cl.

| | |
|---|---|
| ***A61B 17/34*** | (2006.01) |
| ***A61B 17/00*** | (2006.01) |
| *A61B 17/06* | (2006.01) |

(52) U.S. Cl.

CPC .... *A61B 17/3423* (2013.01); *A61B 17/00234* (2013.01); *A61B 17/3498* (2013.01); *A61B 2017/00243* (2013.01); *A61B 2017/06019* (2013.01); *A61B 2017/3419* (2013.01); *A61B 2017/3425* (2013.01); *A61B 2017/3464* (2013.01)

(58) Field of Classification Search

CPC .......... A61B 17/3423; A61B 17/00234; A61B 17/3498; A61B 2017/00243; A61B 2017/0609; A61B 2017/3419; A61B 2017/3425; A61B 2017/3464; A61M 60/861; A61M 60/863; A61M 39/06

See application file for complete search history.

(56) References Cited

U.S. PATENT DOCUMENTS

| | | | |
|---|---|---|---|
| 5,085,636 | A | 2/1992 | Burns |
| 5,492,304 | A | 2/1996 | Smith et al. |

(Continued)

FOREIGN PATENT DOCUMENTS

| | | | |
|---|---|---|---|
| RU | 2 696 685 | C1 | 8/2019 |
| WO | WO2011/017440 | A2 | 2/2011 |
| WO | WO2018/167059 | A1 | 9/2018 |

OTHER PUBLICATIONS

WIPO, European International Search Authority, International Search Report and Written Opinion mailed Jul. 28, 2021 in International Patent Application No. PCT/EP2020/088064, 19 pages.

(Continued)

*Primary Examiner* — Diane D Yabut

(74) *Attorney, Agent, or Firm* — Inskeep IP Group, Inc.

(57) ABSTRACT

An access device for a heart chamber, a removable hemostatic valve unit, and a system including a cardiac assist unit are disclosed. In examples, the access device) includes an apical base plate and a sealing unit configured to provide a separation of a wet zone from a heart chamber and a dry zone with a gaseous environment outside of said heart chamber inside a patient body at the same time.

13 Claims, 24 Drawing Sheets

Related U.S. Application Data is a continuation of application No. 16/990,903, filed on Aug. 11, 2020, now Pat. No. 12,478,403, which is a continuation of application No. PCT/EP2019/087182, filed on Dec. 30, 2019.

(56) References Cited

U.S. PATENT DOCUMENTS

| | | | | |
|---|---|---|---|---|
| 2004/0092965 | A1* | 5/2004 | Parihar .............. | A61B 17/0057 606/144 |
| 2006/0217666 | A1 | 9/2006 | Wenchell | |
| 2011/0118766 | A1 | 5/2011 | Reichenbach et al. | |
| 2011/0251450 | A1 | 10/2011 | Pagani et al. | |
| 2012/0059212 | A1 | 3/2012 | LaRose et al. | |
| 2012/0165931 | A1 | 6/2012 | Bourque | |
| 2012/0296151 | A1 | 11/2012 | Curtis et al. | |
| 2014/0171873 | A1* | 6/2014 | Mark ................. | A61B 17/3417 604/164.01 |
| 2016/0081715 | A1 | 3/2016 | Kleyman | |
| 2016/0151552 | A1 | 6/2016 | Solem | |
| 2018/0036034 | A1 | 2/2018 | Williams et al. | |
| 2019/0269839 | A1 | 9/2019 | Wilson et al. | |

OTHER PUBLICATIONS

WIPO, European International Search Authority, International Search Report and Written Opinion mailed Sep. 23, 2020 in International Patent Application No. PCT/EP2019/087182, 17 pages.
WIPO, European International Search Authority, Invitation to Pay Additional Fees including Partial International Search Results and Provisional Opinion mailed Jul. 29, 2020 in International Patent Application No. PCT/EP2019/087182, 17 pages.

* cited by examiner

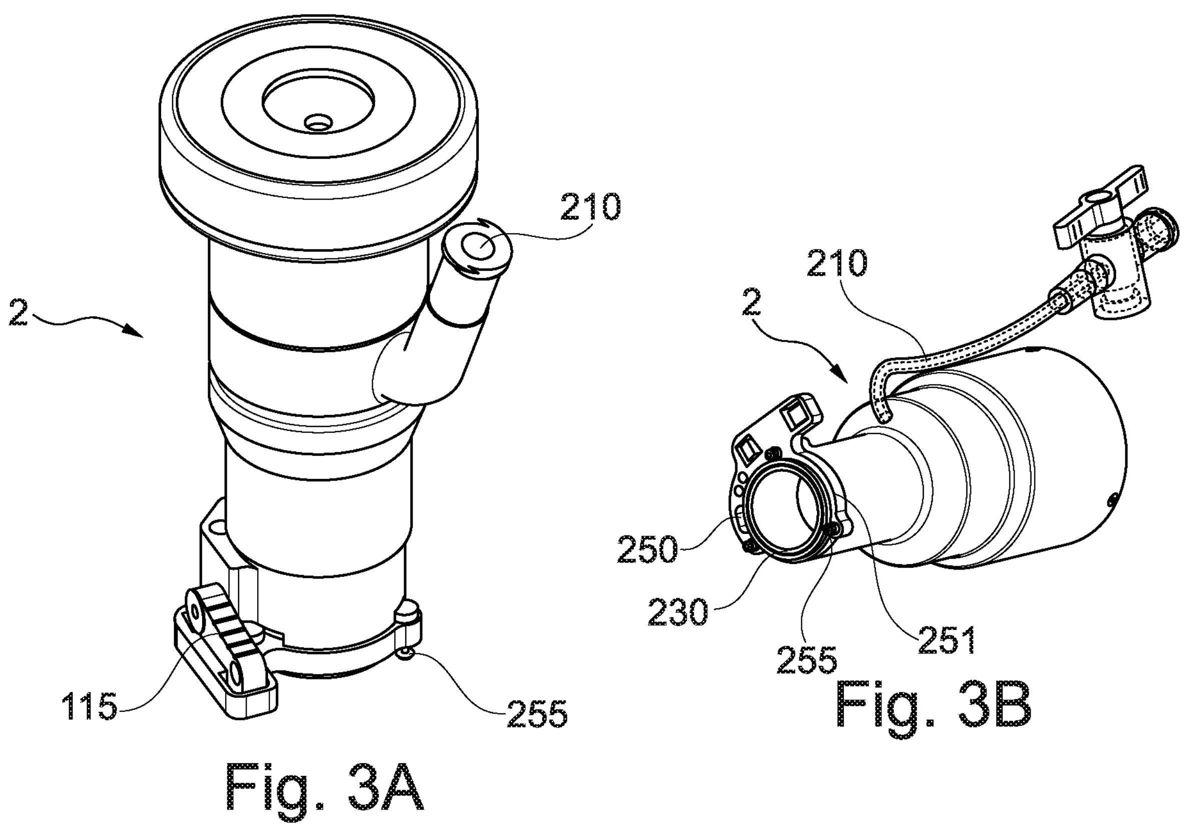
Fig. 3A
Fig. 3B
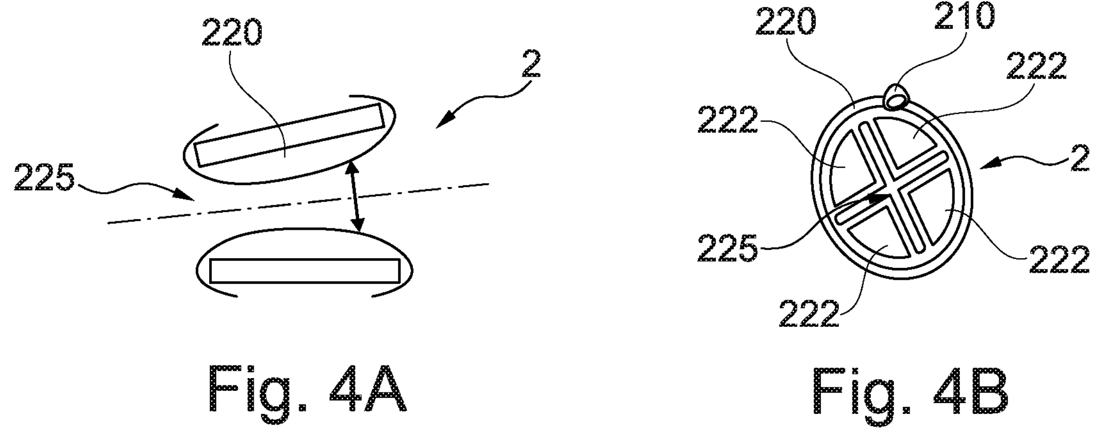
Fig. 4A
Fig. 4B

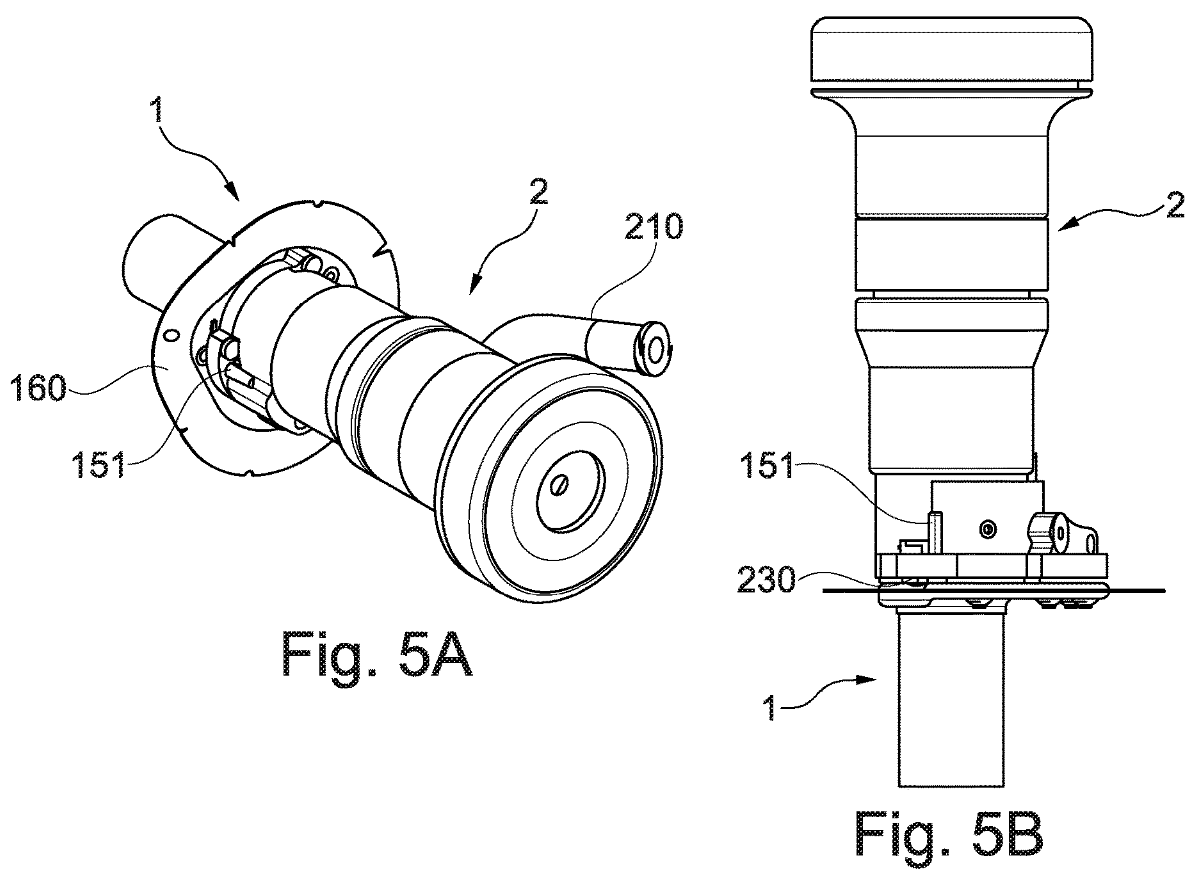
Fig. 5A
Fig. 5B
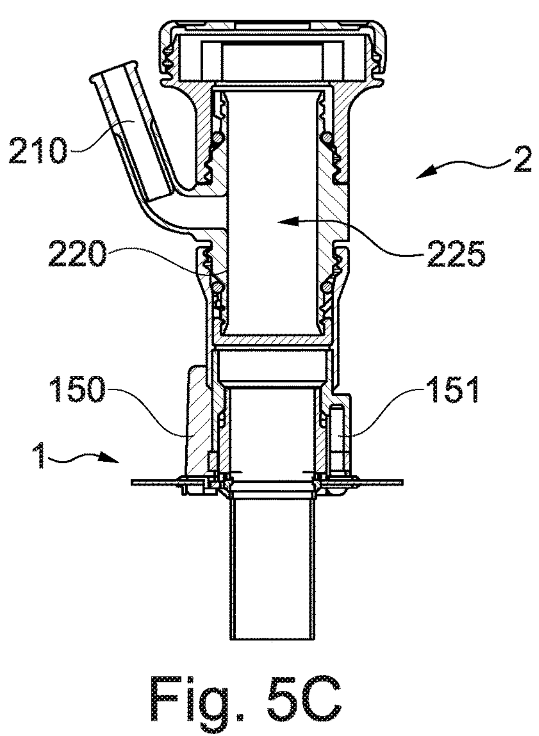
Fig. 5C 10
12

10
472
460
410

10
472
475
410

7
74
72
2
70
1

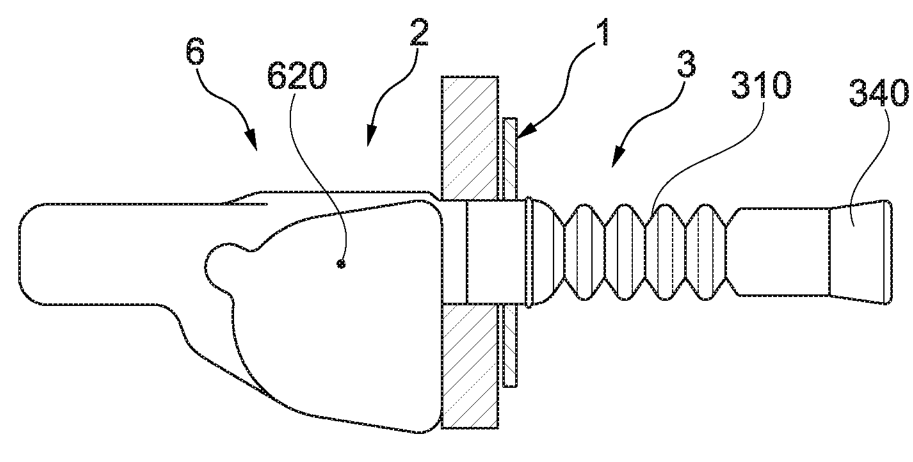
Fig. 24A
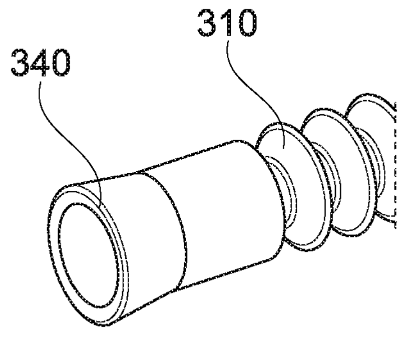
Fig. 24B
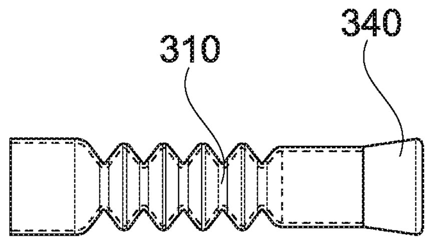
Fig. 24C
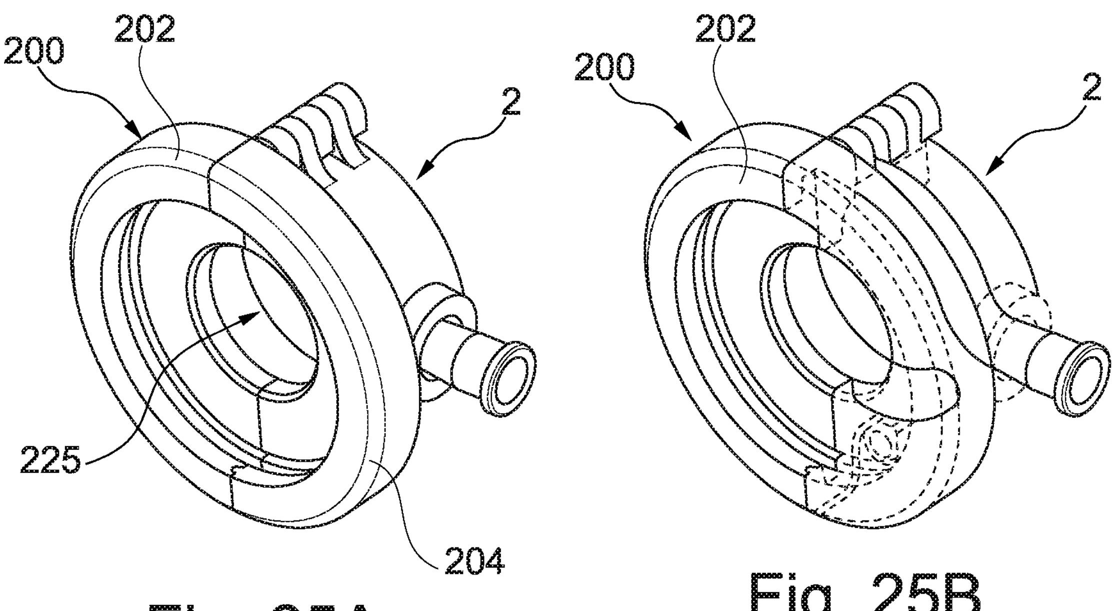
Fig. 25A
Fig. 25B

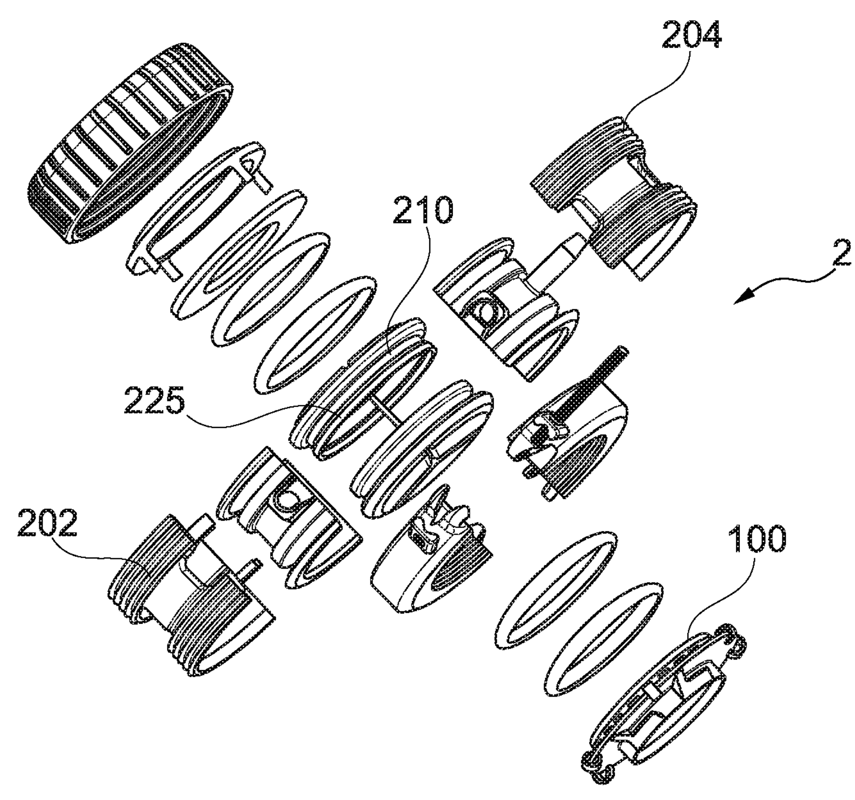
Fig. 25E
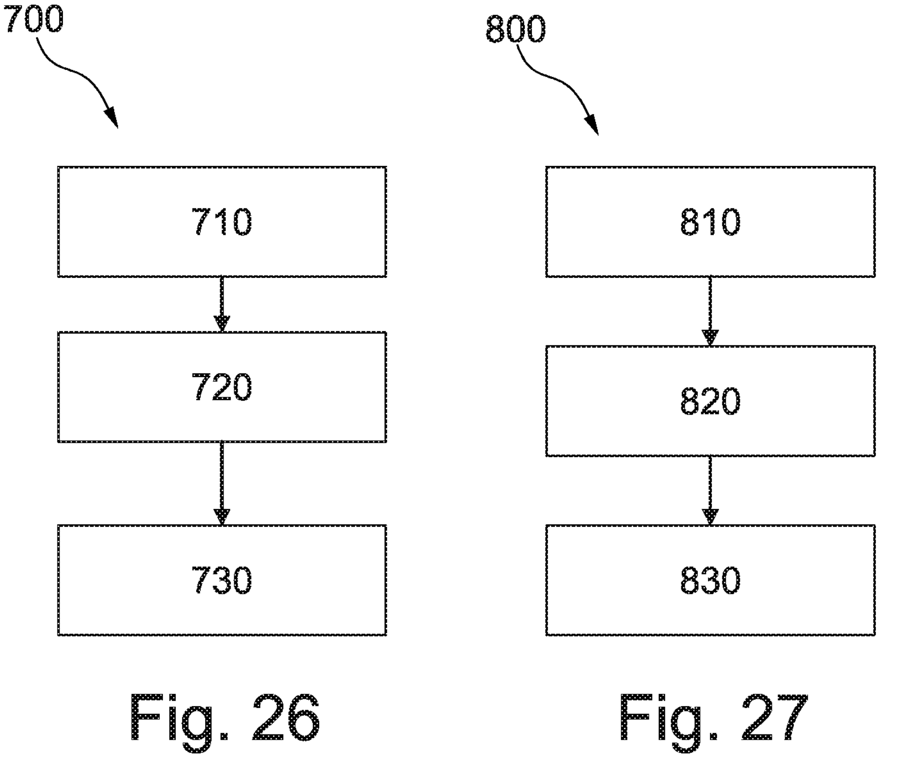
Fig. 26
Fig. 27

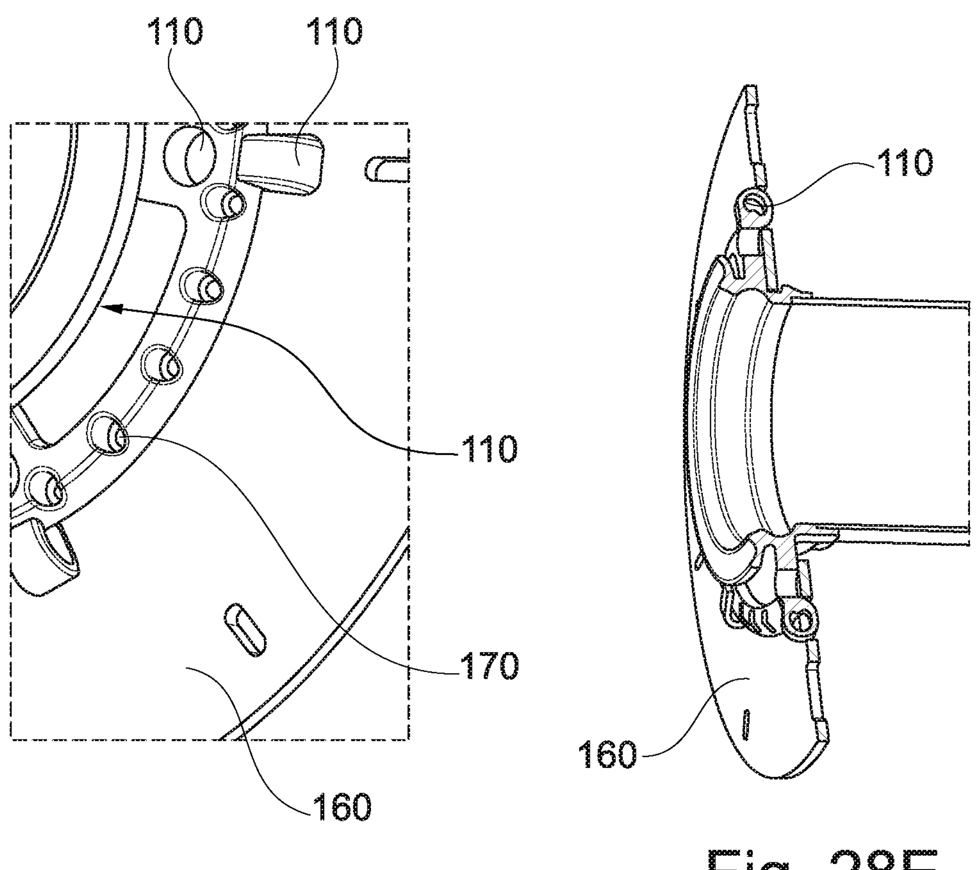
Fig. 28D
Fig. 28E
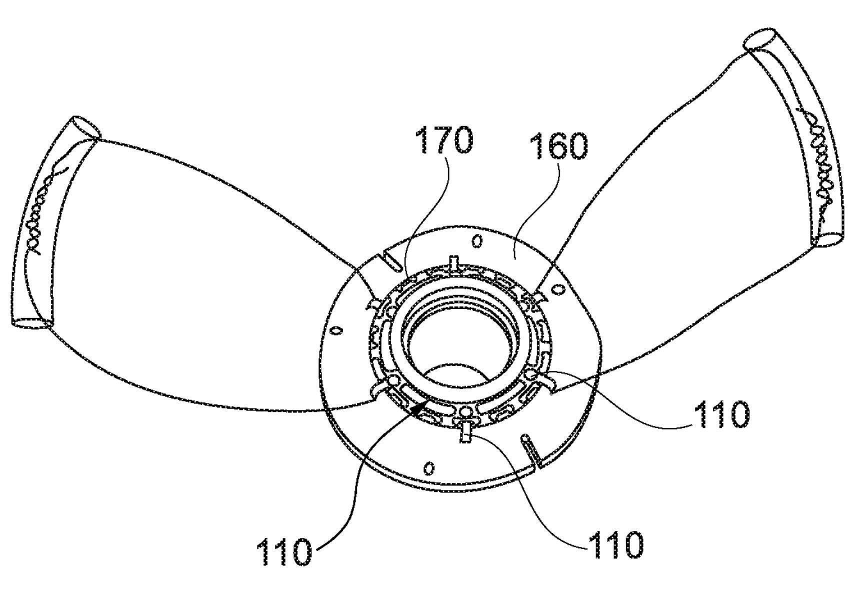
Fig. 28F

INTERFACE FOR ACCESSING THE INTERIOR OF A HEART

RELATED APPLICATIONS

This application is a bypass continuation of and claims priority to International Patent Application No. PCT/EP2020/088064, International Filing Date Dec. 30, 2020, entitled An Access Device For A Heart, A Removable Hemostatic Valve Unit, And A System Including A Cardiac Assist Unit, which claims priority to U.S. application Ser. No. 16/990,903 filed Aug. 11, 2020 entitled An Access Device For A Heart, A Removable Hemostatic Valve Unit, And A System Including A Cardiac Assist Unit, which is a bypass continuation of and claims priority to International Patent Application No. PCT/EP2019/087182, International Filing Date Dec. 30, 2019, entitled An Access Device For A Heart, A Removable Hemostatic Valve Unit, And A System And A Method Of Creating A Transapical Passage On A Beating Heart, all of which are hereby incorporated herein by reference in their entireties.

BACKGROUND OF THE INVENTION

Field of the Invention

This disclosure pertains in general to the field of cardiac medical devices. More particularly the disclosure relates to access devices for a heart, in particular transapical access devices being transapical ports to and from a heart's chambers. Also, the disclosure relates to hemostatic valve units, in particular hemostatic valve units for delivery of medical devices via a cardiac apex to a heart, and even more particularly to such hemostatic valve units with variable orifices and preferably removable from the heart after use. In addition, the disclosure relates to medical procedures, methods and systems of and for creating a transapical passage on a beating heart. Moreover, the disclosure relates to medical systems including cardiac assist units to be transapically implanted. Furthermore, the disclosure relates to apical base plates including a connection interface. In addition, the disclosure relates to medical procedures, methods and systems of and for transapically implanting a cardiac assist system.

Description of Prior Art

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In international patent publication number WO2009100198A2, transapical heart ports, methods for making transapical heart ports, and methods for using transapical heart ports are provided. However, these heart ports may be further improved.

In British patent specification number GB1514019 a hemostatic valve with a fluid pressure controllable cross section is disclosed. However, these hemostatic valves may be further improved.

In international patent publication WO 2018/167059 A1, a transapical heart port is disclosed. The heart port is for use during cardiac surgery to access the interior of a heart via its apex. The heart port is removed after the surgical procedures are performed (page 8 lines 9 to 10). During the procedure it has a hemostatic valve attached to its housing, more precisely it is screwed onto the proximal part of the port. The valve is not disclosed as removable during use. The valve cannot be removed, i.e. disassembled, from the port during use as this would cause undesired blood loss. The port is also not disclosed providing a dry zone in the patient when permanently implanted (i.e. surgery is ended, and the patient body is closed again) as it is removed from the patient.

In international patent publication WO 2011/017440 A1, organ ports are disclosed, such as transapical heart ports and methods and materials for implanting such organ ports. The ports are for use during medical surgical procedures and can include a hemostatic valve attached to a housing of such port and located within a channel for instance to reduce blood loss from a heart through the channel. However, such ports are not disclosed providing a dry zone in the patient when permanently implanted (i.e. surgery is ended, and the patient body is closed again).

In United States Patent Application Publication US 2016/0081715 A1, a surgical access device is disclosed for introduction of surgical instrumentation into a patient's body. The device includes a lateral moving seal cooperating with a bellows. The bellows is arranged between an inner and an outer seal housing and establishes a biasing relationship with the seal. The device is not suited for permanent implantation, e.g. for use with a cardiac assist device. It is also not suited as a cardiac transapical heart port.

A similar seal assembly with a bellows is disclosed in U.S. Pat. No. 5,492,304. A bellows allows reduction of the overall axial dimension of the seal assembly. However, the device is not suited for permanent implantation, e.g. for use with a cardiac assist device. It is also not suited as a cardiac transapical heart port.

For instance, it would be desired to provide a permanent separation of a wet zone from a heart chamber and a dry zone with a gaseous environment outside of said heart chamber inside a closed patient body at the same time.

A transapical access device is desired that prevents blood leakage while working on a beating heart and which allows for attachment of other units than hemostatic valves, and in particular, other units that have a larger dimension than an opening of a through channel in a hemostatic valve.

It is also desired to be able to transfer a movement longitudinally across the apex without bleeding and easy installation of a sealing unit at the apex.

Another desired property is that access to a heart chamber at a later point is facilitated, e.g. for repair or replacement of components installed inside the heart.

SUMMARY OF THE INVENTION

Embodiments of the present disclosure preferably seek to mitigate, alleviate or eliminate one or more deficiencies, disadvantages or issues in the art, such as the above-identified, singly or in any combination by providing devices, systems and methods according to the appended patent claims.

The present invention is defined by the appended claims only, in particular by the scope of appended independent claim(s). Reference(s) to "embodiments" throughout the description which are not under the scope of the appended claims merely represents possible exemplary executions and are therefore not part of the present invention.

According to aspects of the disclosure, access devices for a heart, removable hemostatic valve units, a system and a method of creating a transapical passage on a beating heart, and a method of transapically implanting a cardiac assist system are provided, medical systems including cardiac assist units to be transapically implanted, and apical base plates, are provided herein. An apical base plate is a plate for attachment to an apex region of a heart.

As mentioned above, this document relates to medical devices. For example, this document provides transapical heart ports and methods for using transapical heart ports. The transapical heart ports provided herein can be inserted and secured to the apex of a beating heart to provide secure access to the inside or interior of the heart. The devices provided herein provide access to the inside of the heart via the apex without blood loss around instruments being introduced into the heart. The transapical heart ports provided herein can be used during surgeries where the patient's heart remains beating. The transapical heart ports provided herein can be used for inserting instruments of various types into the heart. For example, annuloplasty rings, artificial valves, valve clips, cardiac assist components, can be inserted into the heart, such as by using an exemplary delivery system 7 shown in FIGS. 20A and 20B.

In examples, the access device includes an apical base plate and a sealing unit 3 configured to provide a separation of a wet zone 30 from a heart chamber 20 and a dry zone 32 with a "gaseous environment" such as outside of said heart chamber inside a patient body at the same time, as defined below.

The sealing unit 3 is not included in a hemostatic valve, or part of a hemostatic valve but rather a separate entity, as elucidated herein.

In some cases, a transapical heart port provided herein can be inserted at the apex of the heart, for example, using an open surgical incision or percutaneously. In some cases, a transapical heart port itself can provide secure access such that instruments can be exchanged during the intracavitary surgery without concern that one would lose control of the apex of the heart (e.g., to prevent bleeding through or around the transapical heart port and to maintain blood pressure in the patient).

The transapical heart port provided herein is intended to remain permanently implanted in place after completion of the operation being performed on the heart. A sealed access to the interior of the heart is provided in some configurations.

The access device 1 has for instance in examples a first, open patient (body) configuration. An open patient configuration means that the patient body is opened for a surgical procedure, often by a section through the patient skin, and during the surgical procedure—in contrast to a closed patient (body) configuration. In the example of the open patient body configuration, a removable hemostatic valve unit 2 is removably attached to a proximal side of said apical base plate 100. In the first configuration, examples include that only the hemostatic valve unit 2 is mated with the apical base 100.

The access device 1 has for instance in examples a second, closed patient (body) configuration, A closed patient (body) configuration means that the patient body is closed after conclusion of the surgical procedure. In the closed patient configuration, the sealing unit 3, that optionally includes a feed-through port 320, is preferably distally attached to said base plate 100 for providing the separation of wet and dry zones. In the first configuration, examples include that the sealing unit 3 is mated with the apical base 100.

In a third configuration of the access device 1, both the hemostatic valve unit 2 and the sealing unit 3 are mated to the apical base 100. This third configuration is also an open patient (body) configuration. A transition configuration from the first to the second configuration may include the sealing unit 3 inserted into the hemostatic valve unit 2 for delivery to the apical base plate 100.

The access device, including the apical base plate (100) includes preferably a tubular through port 120 adapted to be arranged across cardiac tissue.

According to one aspect of the disclosure, access devices for a heart are provided. The devices include an apical base plate that has a tubular through port to be arranged across cardiac tissue. "Across" means in the present context through cardiac tissue and between an inside and an outside of the heart. The cardiac tissue at the apex is thus provided with a tubular port extending from the outside of the heart tissue to the inside of a heart chamber at the apex region of the heart. This port can be to/from the left or the right chamber.

The access device has a first configuration wherein a removable hemostatic valve unit is attached to the base plate. The port is thus open for fluid communication and is closable to prevent bleeding, controllable by the valve.

Advantages of a removable hemostatic valve include for instance one or more of the following technical effects. It prevents blood leakage while working on a beating heart. Being removable, it allows for attachment of other units than hemostatic valves—instead of the valve but also in addition to the valve before removal of the valve. Other units can have a larger dimension than an opening to a through channel in the hemostatic valve, in particular if the valve housing is provided as splittable for providing a peel off valve. It may be a re-usable valve. It may be re-attached if needed. In particular if the re-attached valve housing is provided as splittable for providing a peel on valve. It provides for attachment of a driving unit in a transition configuration of a drive unit, valve, base plate, sealing unit. It provides for temporary sealing of a cardiac access channel, e.g. for installing examples of a permanent sealing unit 3 that is adapted to remain implanted. It provides for creation of a wet dry zone separation. A re-attachable hemostatic valve, e.g. in the form of a peel on valve, provides the possibility to exchange, replace, reposition, repair, and/or improve single and/or multiple components or entire modules such as a bellows 310 or products such as a drive unit of a cardiac support system. An example of a removable and re-attachable hemostatic valve is seen in FIGS. 25A to 25E. In FIG. 25A or 25D examples is a hemostatic valve are illustrated in assembled state and FIGS. 25B, 25C and 25E show examples of a hemostatic valve illustrated in dissembled state, respectively. Parts 202, 204 illustrate some of the splittable parts of the hemostatic valve.

A "wet dry zone" as used in this disclosure includes a separation of a wet zone, i.e. containing blood, in a heart chamber, from a dry zone, i.e. a gaseous or in particular air containing environment, such as outside of the heart chamber, but in any case inside an intact human body, at the same time.

The gaseous environment may for instance be provided outside of the heart chamber, see an example illustrated in FIG. 23 with a gaseous environment inside the drive unit 6.

Additionally, or alternatively, the gaseous environment may be provided inside the heart chamber, sealed from the wet zone, see e.g. FIG. 11C or FIG. 23, where the sealing unit 3 has a gaseous environment in its interior securely sealed from the blood in the chamber, i.e. away from the wet zone.

Additionally, or alternatively, the gaseous environment may be provided inside the transapical hole, see e.g. FIG. 11C or FIG. 23, where the sealing unit 3 provides for a gaseous environment inside the transapical hole.

Alternatively, or in addition, the gaseous environment may at least partly contain a liquid to provide a "gaseous" environment containing a medium different than blood, such as a biocompatible lubricant medium e.g. for mechanical parts to enhance operational life, and/or a protective gas, or a mixture thereof, such as aerosol particles in gas. As long as the "gaseous" environment of the dry zone is securely sealed inside the patient body from the wet zone containing blood, it is a "gaseous" environment as used in this disclosure.

The wet dry zone is thus providable during permanent implantation of a medical device, such as an apical base plate, in a closed patient's body.

The access device has a second configuration wherein a sealing unit with a feed-through port 320 is attached to the base plate. The feed through port is provided with separation of the wet zone and dry zone. A membrane, like including a silicone (or other synthetic material like PVC, Polyurethane, etc.) bellow is provided for separating the wet zone from the dry zone. The membrane may consist of more than one membrane or bellow in order to create a membrane in membrane solution or bellow in bellow solution. The different bellows, in a bellow in bellow solution, may consist of different materials. The different materials may have different properties, like different permeability of particles. In this way, a more efficient "total" membrane may be costumed and/or created. The different bellows may also consist of the same material, e.g. in order to create an extra safety if one bellow may break and/or leak. This may prevent gas leakage from dry zone into blood stream. The feed-through port means that devices may cross the dry zone to/from the wet zone. The feed through port 320 is for instance provided at the distal end portion of the sealing unit 3. A sealing member, like an O-ring, 326 may be provided to provide sealing at the feed through port. Alternatively, the feed through port may be without a sealing member but a closed membrane, e.g. for magnetic couplings as shown in FIGS. 24A, 24B and 24C. In this second configuration, the port is closed for fluid communication by means of the sealing unit. A feed-through port, e.g. for medical devices is however provided in this configuration. The sealing unit provides for the wet/dry zone separation.

Some examples of the sealing unit 3 provide for a possible movement of mechanical parts via/across the apex and a separation of a wet zone, e.g. blood in heart chamber, and a dry zone, i.e. gaseous/air environment outside of heart chamber, at the same time without leakage of blood or gas over the separation by e.g. a membrane for instance including a bellows 310. Such a sealing unit 3 may include a detaining unit 330 to provide a detainment of blood and/or gas in order to delay and/or prevent an exchange of blood or gas over the separation e.g. in case of a membrane malfunction. In examples, the detaining unit may delay and/or prevent a leakage of blood or gas over a membrane if for instance a bellows 310 would break or malfunction. In examples, the detaining unit is a sponge, or consists of sponge-like material, which allows for slow or inhibited leakage of gas into blood, or vice versa. In other examples, the detaining unit may include a three-dimensional maze that allows for gas to freely pass through but can provide a delay and/or entirely prevent blood from passing through the maze. The detaining unit may be positioned inside the sealing unit 3. For instance, the interior channel of the bellows 310 may be provided with the detaining unit. Alternatively, or in addition, the detaining unit may be provided in the top of the sealing unit 3 (when assembled positioned in tubular through port 120), see e.g. in the interior space of the tubular through port 120 inside sealing unit 3 such as illustrated in FIG. 22B. A detaining unit consisting of a maze would provide a detainment of blood causing a detainment of gas and thus would delay and/or prevent an exchange of blood or gas over the separation. In other examples, the detaining unit may provide a controlled leakage and/or dissolvement of gas in blood, or vice versa, due to the costumed design of the detaining unit. The detaining unit may be constructed as a diffusor for spreading gas into liquid in a controlled way, e.g. in order to dissolve in blood. The detainment unit improves patient safety as it avoids or slows down potential gas leakage into the blood stream of the patient, or as it avoids, or slows down potential blood leakage into the device. In this context it should be noted that small amounts of gas released over time are either not harmful or can be dissolved in the blood, which is not critical for the patient. On the other hand, the same amount of gas released instantaneously could be life threatening, but this is avoided by the detaining unit.

A sealing unit with bellows allows for a, e.g. longitudinal and/or axial, movement of medical device parts relative each other, e.g. for piston or rods' movements. A sealing unit with bellows allows in addition or alternatively for radial movement of device parts relative each other, in particular from outside the heart to the inside of the heart, while the wet/dry separation is maintained.

The sealing unit provides in an advantageous manner a separation of a wet zone from a dry zone.

The sealing unit may be provided with a magnetic coupling, as shown in an example in FIGS. 24A, 24B and 24C. A magnetic coupling provides for easy assembly of components of a system to be implanted, and/or easy detachment of components such as for replacement, addition, removal or repair of such components. It provides for a total sealing of the feed through port without a through channel.

According to another aspect of the disclosure, a hemostatic valve unit is provided. The valve unit has a housing with a distal end and a proximal end. It is removably connectable at the distal end to an apical base plate of an access device for a heart. The valve unit includes a pneumatic valve in a through channel of the valve unit between the distal end and the proximal end. The valve is reattachable if needed, e.g. for later access such as for replacing/repairing components of a cardiac assist system. Advantages of a removable valve are already described above and also apply for this aspect.

According to yet another aspect of the disclosure, applicator tools are provided for creating a transapical passage on a beating heart. The applicator tool (in short herein referred to as the "tool") includes in examples a harpoon insertable through a tube of the applicator tool. The harpoon has a distal tip for penetrating cardiac tissue at an apex of a heart. The tube has a sharpened edge at a distal end for cutting the cardiac tissue at the apex. The harpoon has an expandable flange for preventing withdrawal of the harpoon through the cardiac tissue, in particular while cutting with the tube and providing a clean cut because it provides in use a counterforce against the tube's cutting edge, wherein the flange is configured to keep the cut cardiac tissue within the tube.

Some examples of the disclosure provide for applicator tools with improved patient safety as embolization of cut cardiac tissue is prevented. The tissue that is cut is safely kept in the tube with the harpoon flanges or wire mesh holding back the tissue in the tube. Complications like stroke are minimized or avoided by such examples of applicator tools for creating a transapical passage on a beating heart, which is a particular challenge because of the heart movements and related difficulties to contain cut tissue and prevent it from being entrained with the blood flow of the beating heart for instance. The tool is advantageous as it provides that leakage of blood from the chamber is prevented when creating a transapical passage. The penetration through the cardiac tissue to the chamber, e.g. at the apex, is recognized by the operator as complete, e.g. by an integrated blood indicator 490. Also, an access device is deliverable over the same tool preparing the puncture, thus a shortened and more safe medical procedure is provided. The tool provides a reproducible desired hole size. The applicator tool avoids undesired, e.g. too large or small cutting of transapical holes. The applicator tool provides for a reproducible medical procedure, in a pre-configured sequence assisting medical personal during implantation. The tool provides for a safe medical procedure with reduced overall patient risk compared to manual cutting of a hole in cardiac muscle tissue with a scalpel.

According to yet another aspect of the disclosure, applicator tools for creating a transapical passage include a harpoon insertable through a co-axial dilator of the tool. The harpoon has a distal tip for penetrating cardiac tissue at an apex of a heart. The dilator provides dilating of the cardiac tissue. The applicator tool furthermore includes an access device for a heart that has a tubular through port to be arranged across the cardiac tissue when advanced over the dilator.

The applicator tool has the same advantages as mentioned above for the previous tool, except tissue that is cut is not kept in the tube with the harpoon flanges or wire mesh holding back the tissue in the tube.

According to yet another aspect of the disclosure, a transapical access system for creating a transapical passage on a beating heart is provided. The system includes an access device for a heart according to the afore described aspect of the disclosure. In addition, the system includes an applicator tool for creating a transapical passage and delivering the access device to an apex of the heart, as described above according to the afore described aspects of the disclosure. The system may provide all or some of the advantages and technical effects of its components described herein.

According to yet another aspect of the disclosure a medical system includes a cardiac assist unit to be transapically implanted. The cardiac assist unit is attachable to a sealed access device. The access device provides for the wet/dry zone separation inside the body. The assist unit is arranged on the dry side. Assembly of the system and implantation is advantageously easy as bleeding is avoided upon and after implantation. As blood cannot enter the assist device, it can be implanted inside the body. Mechanical parts of the assist device arranged in the dry zone are protected from blood, leading to increased time of life, reduced risk for complications, like blood clotting, infections etc. Electronics inside the assist device is protected from short circuits when arranged in the dry zone.

According to yet another aspect of the disclosure, a sealed apical base plate is provided, which includes a connection interface for matingly engagement of multiple medical devices that in turn have mating connection interfaces for connection to the apical base plate, respectively.

The connection interface may include a freely rotatable connection of a system including a medical device relative the apical base plate. Freely rotatable may include three-dimensional movement around a pivot point. Free rotation provides for flexibility for instance when positioning a medical (assist) device during implantation. The free rotation allows for movement of parts relative each other when implanted after ingrowth. This avoids injuries like necrosis e.g. in connecting tissue at the implantation site. Mounting spikes of the base plate are optional and omitted for instance in a free rotation design as these mounting spikes could otherwise prevent the free rotation. The free rotation avoids tension in the implanted system since the devices of the system connected at the connection interface will continuously strive towards a stress-free position. The system has thus a long lifetime and is highly biologically compatible.

According to yet another aspect of the disclosure, a method of creating a transapical passage on a beating heart is provided. The method or medical procedure include determining a position on an apex region for creating a transapical passage. This may for instance be done imaging modality providing suitable image data for processing and analysis, e.g. CT based, MR based, Ultrasonic based. Alternatively, or in addition, the position may be determined by tactile sensing and/or visual inspection of the heart, e.g. during surgery. The method further includes creating a transapical hole at the determined apex region through cardiac tissue, such as by punching and/or cutting through the tissue. The method further includes delivering an access device, such as an apical base plate, which has a tubular through port to the transapical hole. The method further includes attaching a flange unit of the access device to an outside of the heart, and removably connecting a hemostatic valve unit to the access device. The method provides for an advantageous creation of a wet zone/dry zone separation inside a body. The method provides for ease of access to a heart chamber for various procedures and/or medical devices. The method and related devices provide for safe creation of a passage through cardiac tissue, e.g. a transapical passage, while preventing embolies of tissue removed for the passage, e.g. of a punched hole through cardiac tissue. The method and used devices effectively prevent bleeding. The method and used devices provide for reproducible hole sizes. The method and used devices avoid too large cutting of transapical holes, which is an issue difficult to remedy. A reproducible medical procedure is provided as the method needs to be done in a pre-configured sequence, as given by the devices used, assisting medical personal during implantation. Overall, the method provides for a safe medical procedure with reduced risk for patients.

According to yet another aspect of the disclosure, a method of transapically implanting a medical device like a cardiac assist system on a beating heart is provided. The method or medical procedure includes attaching the medical device like a cardiac assist unit to a sealed access device. The medical device like an assist unit is removably attached to the sealed access device, which has a number of advantages. For instance, removable devices provide for extended life of the entire implanted system with replaceable and/or repairable units. The implanted system may easily be updated with improved or enhanced future devices. Repeated access to heart chambers is provided through a permanently implanted access device. Also, the removable medical device can be removed when no longer required (patient treatment successful)

Further embodiments are defined in the dependent claims.

BRIEF DESCRIPTION OF THE DRAWINGS

FIGS. 3A-B illustrate a hemostatic valve unit 2;

FIGS. 4A-B illustrate inflatable balloon configurations of hemostatic valve units;

FIGS. 5A-C illustrate a first configuration of the access device 1;

FIGS. 24A-C illustrate an alternative sealing unit with a magnetic coupling;

FIGS. 25A-E illustrate a splittable hemostatic valve unit;

FIG. 26 illustrate steps of an example of a method of creating a transapical passage on a beating heart;

FIG. 27 illustrate steps of an example of a method of transapically implanting a cardiac assist system;

FIG. 28A-F illustrate examples of an apical base plate.

DETAILED DESCRIPTION

Figures 1A, 1B, 2:
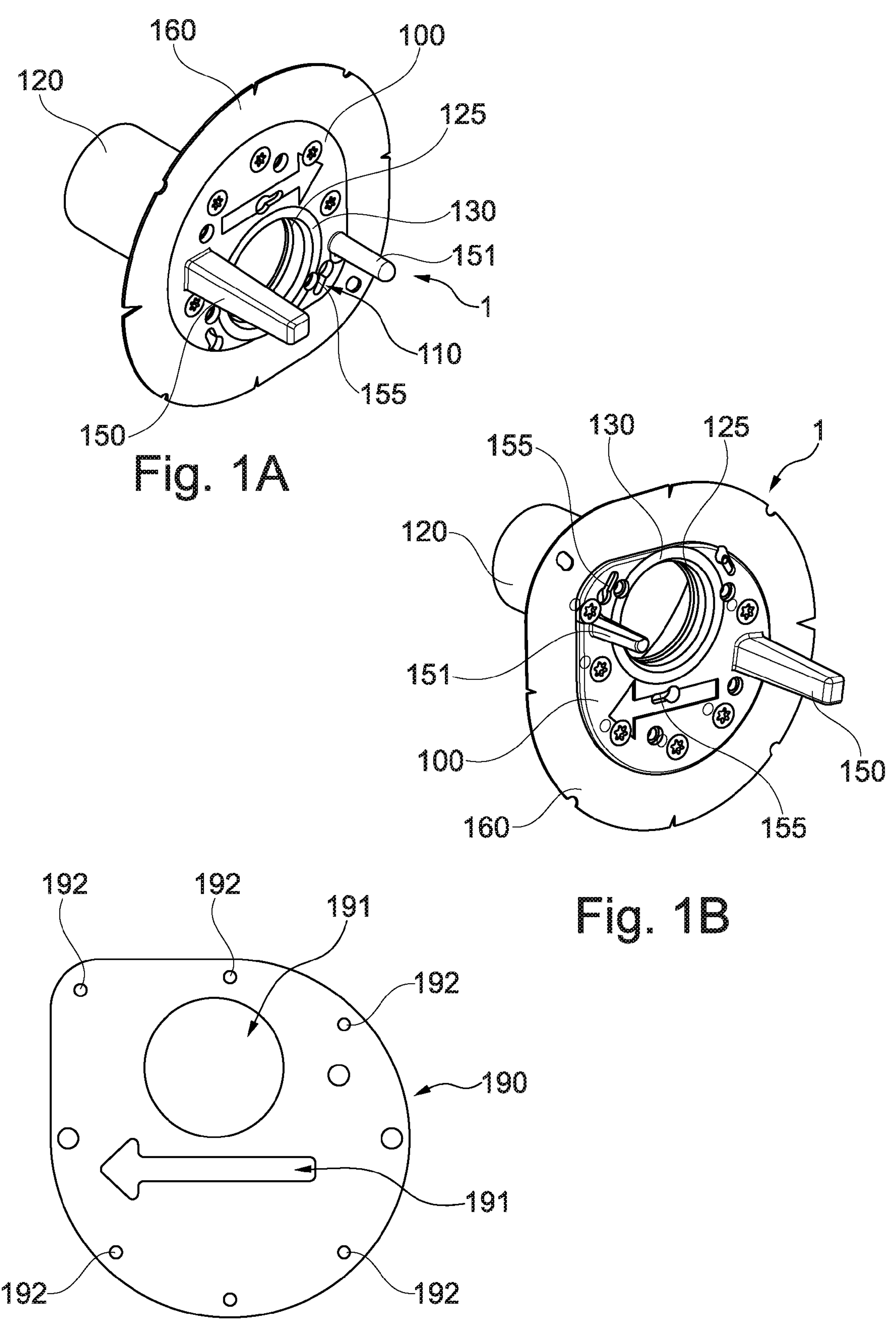
FIGS. 1A-B illustrate an example of access devices for a heart.
FIG. 2 is a top view of a template 190 for positioning an access device 1.

Specific examples of the disclosure will now be described with reference to the accompanying drawings. Inventions comprised herein may, however, be embodied in many different forms and should not be construed as limited to the examples set forth herein; rather, these examples are provided so that this disclosure will be thorough and complete, and will fully convey the scope of an invention to those skilled in the art. The terminology used in the detailed description of the examples illustrated in the accompanying drawings is not intended to be limiting of an invention. In the drawings, like numbers refer to like elements.

Figure 6:
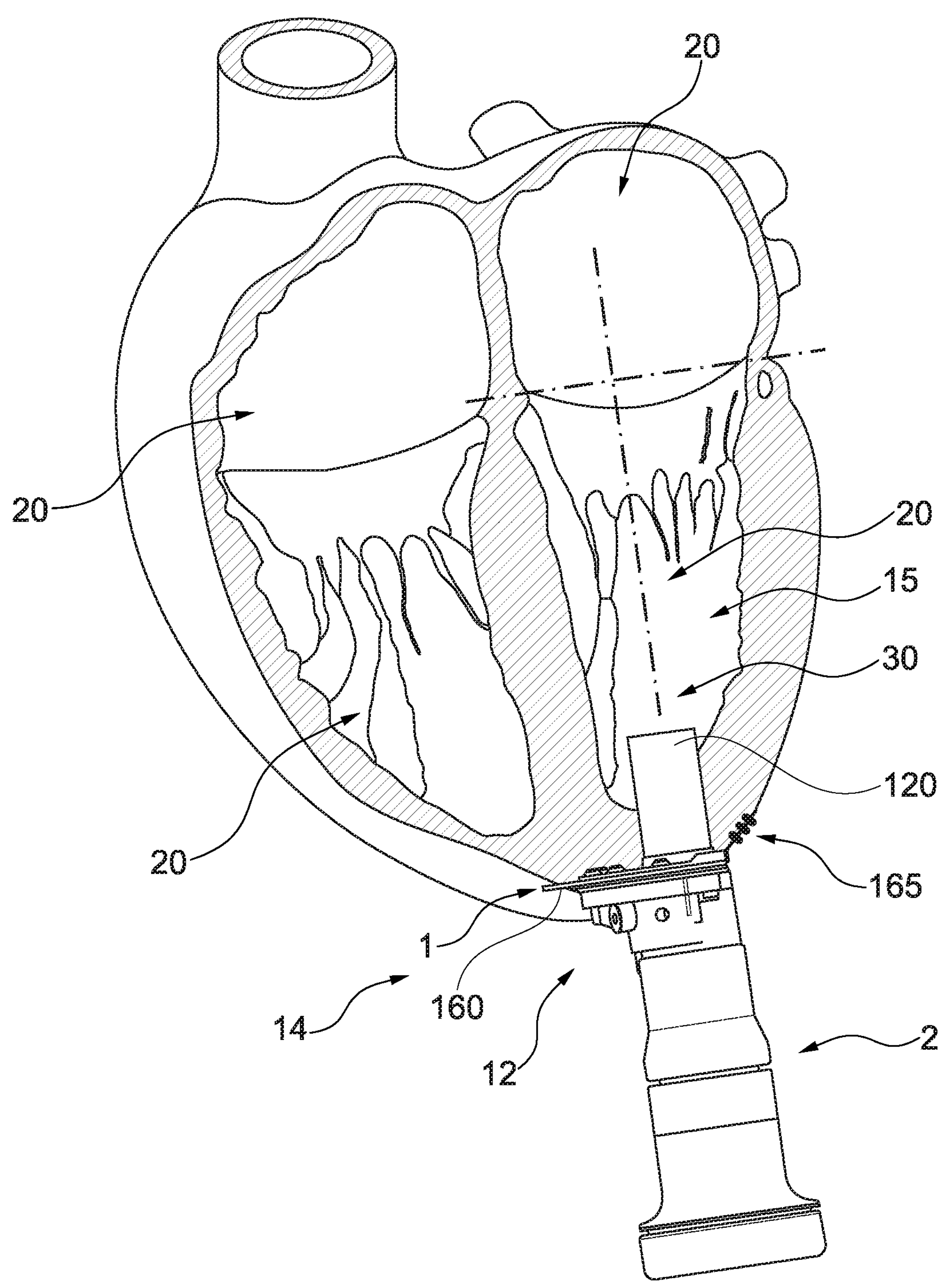
FIG. 6 illustrates an implanted access device 1 in a first configuration.
Figure 7A:
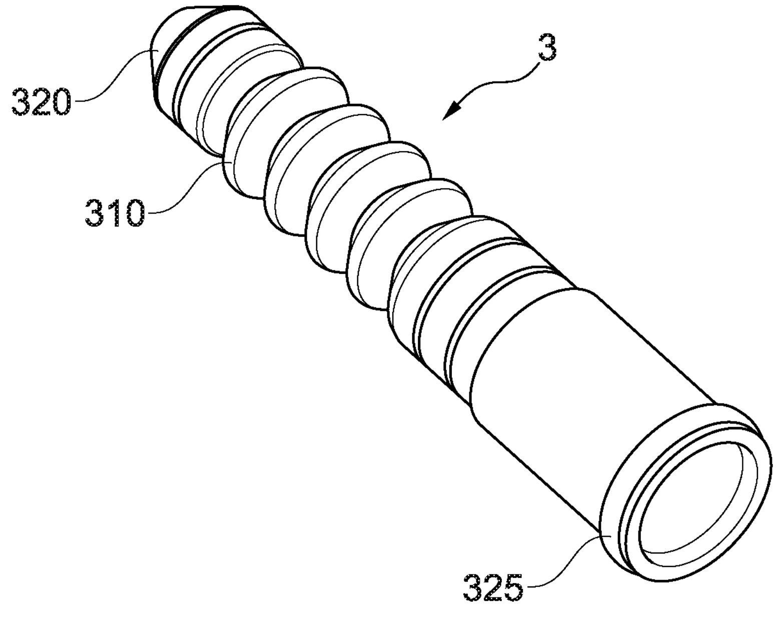
FIGS. 7A-B illustrate a sealing unit for mounting in an access device 1 for providing a second configuration.
Figure 7B:
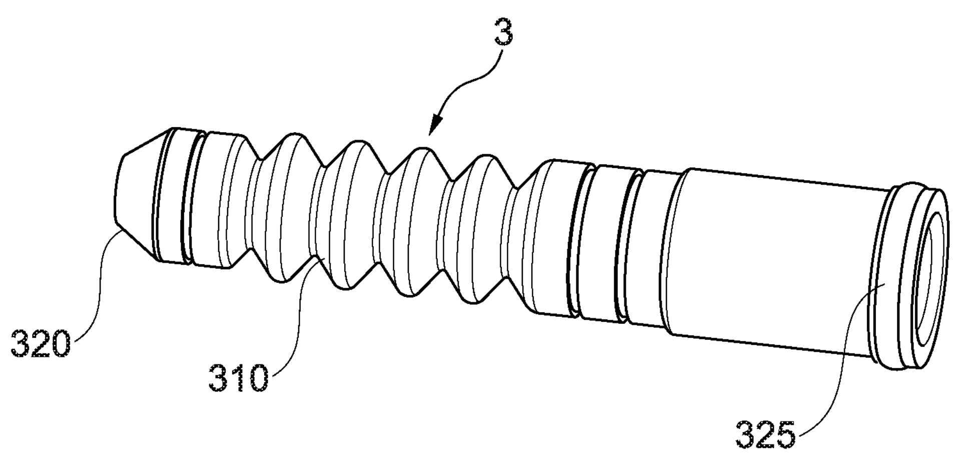
Figure 10A:
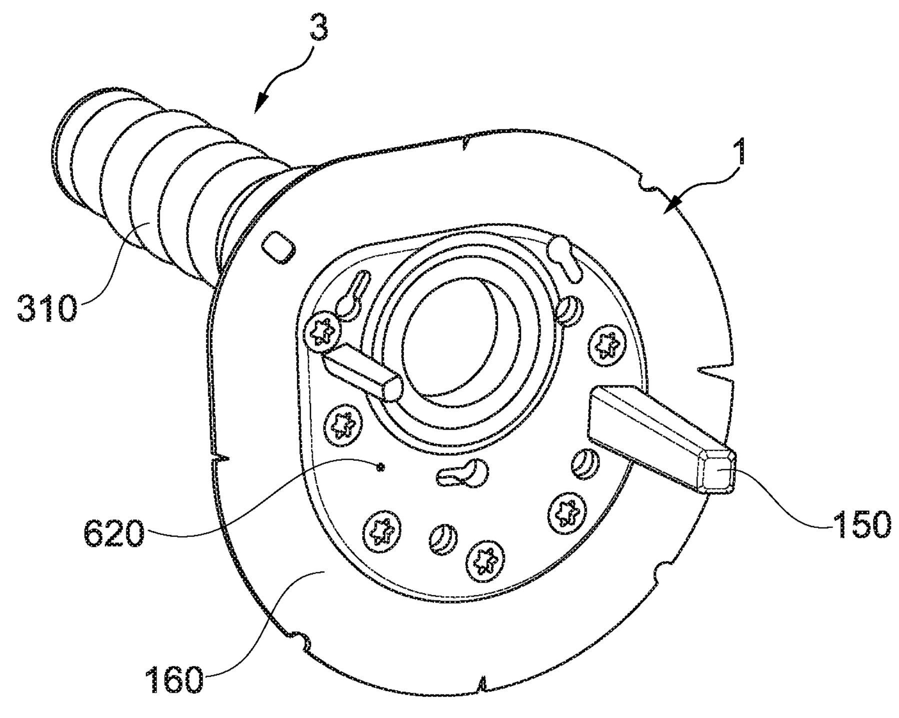
FIGS. 10A-B and 11A-B illustrate a second configuration of the access device 1, in particular an example of a sealed access device 1, which includes a connection interface 110 for matingly engagement of multiple medical devices.
Figure 10B:
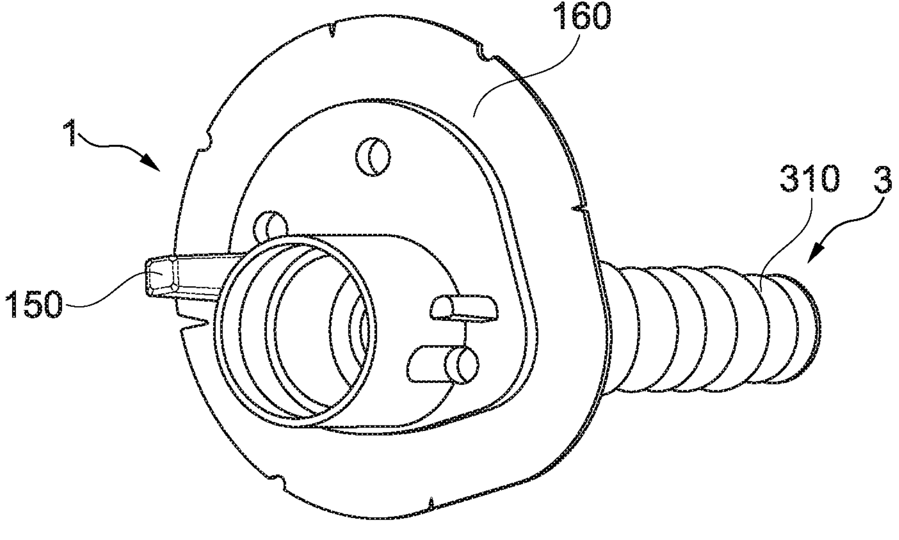

Now turning to the figures, FIGS. 1A and 1B illustrate an example of an access device 1 for a heart, wherein FIGS. 5 and 6 illustrate a first configuration of the access device; and FIGS. 10 and 11 illustrate a second configuration of the access device 1.

The access device 1 include an apical base plate 100 that has a tubular through port 120 to be arranged across cardiac tissue at an apex 12 of a heart 10. The cardiac tissue at the apex 12 is thus provided with a tubular through port 120 extending from the outside 14 of the heart tissue to the inside 15 of a heart chamber at the apex region of the heart 10. This port can be to/from the left or the right chamber of the heart 10, depending on the position at the apex region.

Mounting spikes 150, 151 are provided on the access device for receiving mating apertures or recesses 250, 251 of e.g. a valve unit 2 or a cardiac assist drive unit 6. If having different shape of mating pairs of spikes and apertures, this provides for a rotational correct mounting of units to the access device.

Alternatively, or additionally, locking members may be provided such as bayonet joints 155 to lock units to the access device 1, once mounted thereto or in combination with mounting thereto.

The apical base plate is preferably made of a rigid, preferably biocompatible, material. A flexible flange 160 of the access device 1 allows for attachment to the cardiac tissue at the outside of the heart 10. The flange 160 is for instance made of a biocompatible fabric material, like a woven or nonwoven material. A suitable biocompatible material is for instance Dacron or PTFE. The flange unit 160 is attachable to an outside of the cardiac tissue by suitable attachment elements. The attachment elements are preferably sutures, hooks, clips, staples, and/or screws, etc. The flange includes for example eyelets for receiving sutures for stitching attachment of the access device 1 to the heart. Stitches 165 are schematically illustrated in FIG. 11C. The access device 1 is thus reliable attached to the heart while bleeding from the heart chamber between heart tissue and the tubular through port 120, outside the tube, is prevented by the sealed flange. Bleeding through the tubular through port 120 is prevented initially by the tube 410 while suturing or by the hemostatic valve, when the transapical access system is retracted from the hemostatic valve.

Alternatively, or in addition to using the tool 4 for creating a transapical hole, the hole may be prepared in a conventional surgical procedure using a scalpel. However, this will cause more bleeding than using the tool 4.

The tubular through port 120 is protruding from the apical base plate 100 and plugged into the transapical hole created in a suitable manner. Preferably the tube of the tubular through port 120 has an outer diameter slightly larger than the transapical hole, for improved sealing when in place.

The flange 160 is for instance attached to the apical base plate 100. The base plate may be made of two plates between which the flange can be clamped upon mounting of the plates together (see also FIG. 11B), such as indicated by the screws in the base plate 100 in the illustrating Figures.

Figure 28A:
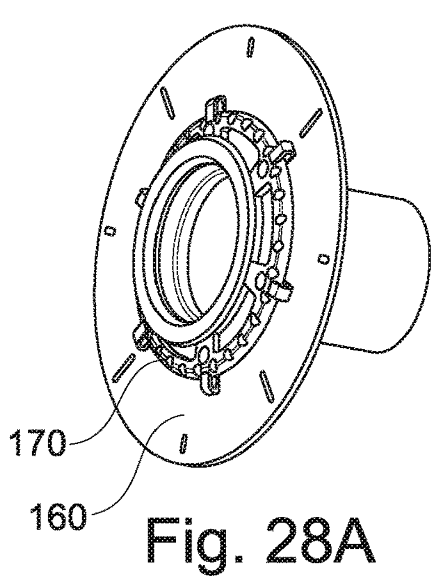
Figure 28B:
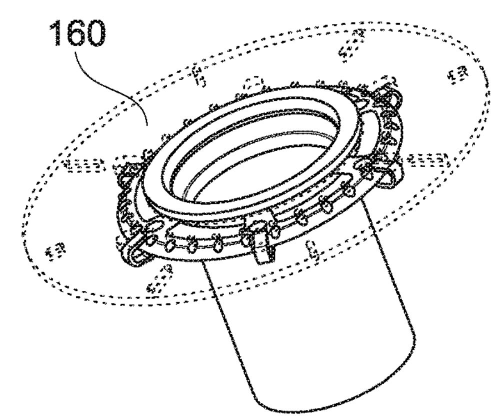
Figure 28C:
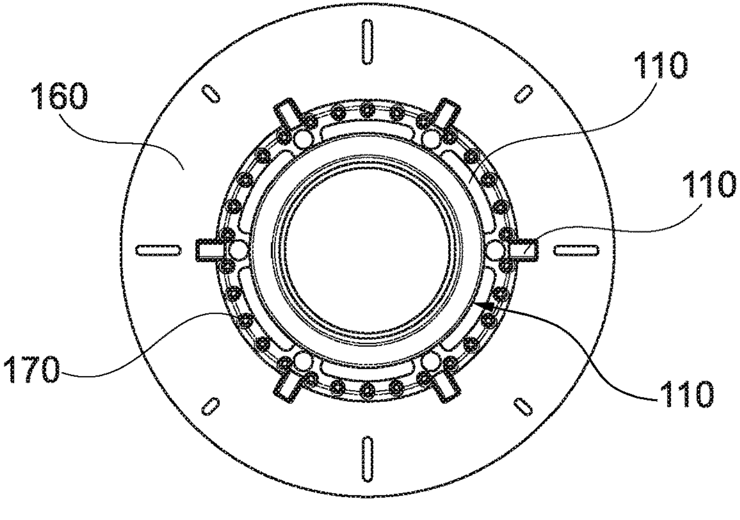

An example of an apical base plate is illustrated in FIGS. 28A, 28B, 28, C, 28D, 28E, and 28F. FIGS. 28A and-28B illustrate the apical base plate. FIG. 28C illustrates a top view of an apical base plate. FIG. 28D illustrated a close-up view of an apical base plate. FIG. 28E illustrates a cross section of an apical base plate. FIG. 28F illustrates an apical base plate having two holders connected thereto.

In the example, the apical base plate comprises suture holes 170 to facilitate attachment therebetween. The flange 160 may be attached to the apical base plate by sutures.

The access device may thus in use be attached to cardiac tissue while sealing the interior from the exterior of the heart. The flange 160 may be sewn to the cardiac tissue, e.g. in a parachute procedure, i.e. the sutures are first fixed to the tissue, e.g. by means of a template 190 at the desire apex location. Then the access device's flange is threaded to the sutures and pushed along the sutures to the cardiac tissue. The access device is then advanced over the tube 410 which occupies the hole on the heart wall until the plate and the flange has contact with the heart surface, and the distal opening of the tube of the tubular through port 120 is inside the heart chamber. The hemostatic valve 2 is connected to the apical base plate 100 during its attachment to the heart. Finally, the sutures are knotted, and the flange 160 is thus tightened to the tissue, such that blood inside the heart does not leak past the access device 1, bleeding through the access device 1 is prohibited by the hemostatic valve. Alternatively, or in addition, to sutures and/or to the parachute procedure described, tissue glue, staples, hooks, clips, or other fixation means may be provided for sealingly affixing the flange 160 to cardiac tissue. The port 120 is the only fluid communication when access device 1 is correctly attached to the apex.

The access device 1 may then be left permanently in place, avoiding the need to close the transapical hole after a surgical procedure. The access device allows for advantageous access to the heart chamber as described herein.

The template 190 shown in FIG. 2 has an exterior perimeter corresponding to the perimeter of the flange unit 160. In this manner, a suitable cardiac surface at the apex can be determined by applying the template 190 to the apex region. The template 190 has markings, e.g. in the form of cut-outs 191, corresponding to elements of the access device 1, e.g. a hole corresponding to the tubular through ports outer diameter. Such cut-outs or similar markings provide that the access device will be oriented correctly at the apex when attached thereto, e-g- by sutures stitched to the cardiac tissue and affixed to the access device 1, e.g. at flange 160. The template 190 preferably includes holes 192 for suture stitching for reliably attaching the access device 1 to the apex at the suitable surface for creating the transapical passage through the cardiac tissue.

Alternatively, or in addition to a template 190, the correct position for implanting the access device 1 may be found manually by tactile sensing of a surgeon and/or imaging, e.g. ultrasonic, based guidance.

The access device 1 has a first configuration wherein a removable hemostatic valve unit 2 is attached to the base plate. The first configuration is illustrated for instance in FIGS. 5A, 5*b* and 5C and FIG. 6. The port 120 is thus open for fluid communication, controllable by the valve 2 when attached thereto. The valve 2 is (re-)attachable or mountable to the base plate 100 by suitable attachment means. For instance, the mounting can be done by threaded attachment (rotation of the devices relative each other), screws, bayonet locks, or similar. The valve 2 is re-attachable removable from the base plate, e.g. at an end of a procedure done through the valve and access device 1, or when the access device 1 has transited to a second configuration where the valve is not needed as for instance sealing is provided by other units such as a sealing unit 3. The removable hemostatic valve 2 has a valve through port with proximal and distal openings providing a communication channel with controllable orifice size, e.g. for delivery of various sized medical device, to and from the interior of the heart (chamber).

The access device has a second configuration wherein a sealing unit 3 with a feed-through port 320 is attached to the base plate 100. The second configuration is illustrated for instance in FIGS. 10A and 10B and FIGS. 11A, 11B and 11C. In this configuration, the port 120 is closed for fluid communication by means of the sealing unit. A feed-through port 320, e.g. for medical devices is however provided in this second configuration of the access device 1. The through port has preferably a sealing 326 to prevent blood from leaking out of the heart. A sealing surface at the tubular through port's inner portion, like at the proximal end illustrated e.g. in FIGS. 1A and 1B, may provide sealing against a sealing member 325, such as at the outside of the sealing unit, e.g. at its proximal end. This prevents blood leakage through the through port when the sealing unit 3 is inserted and affixed to the access device 1.

Figures 8A, 8B:
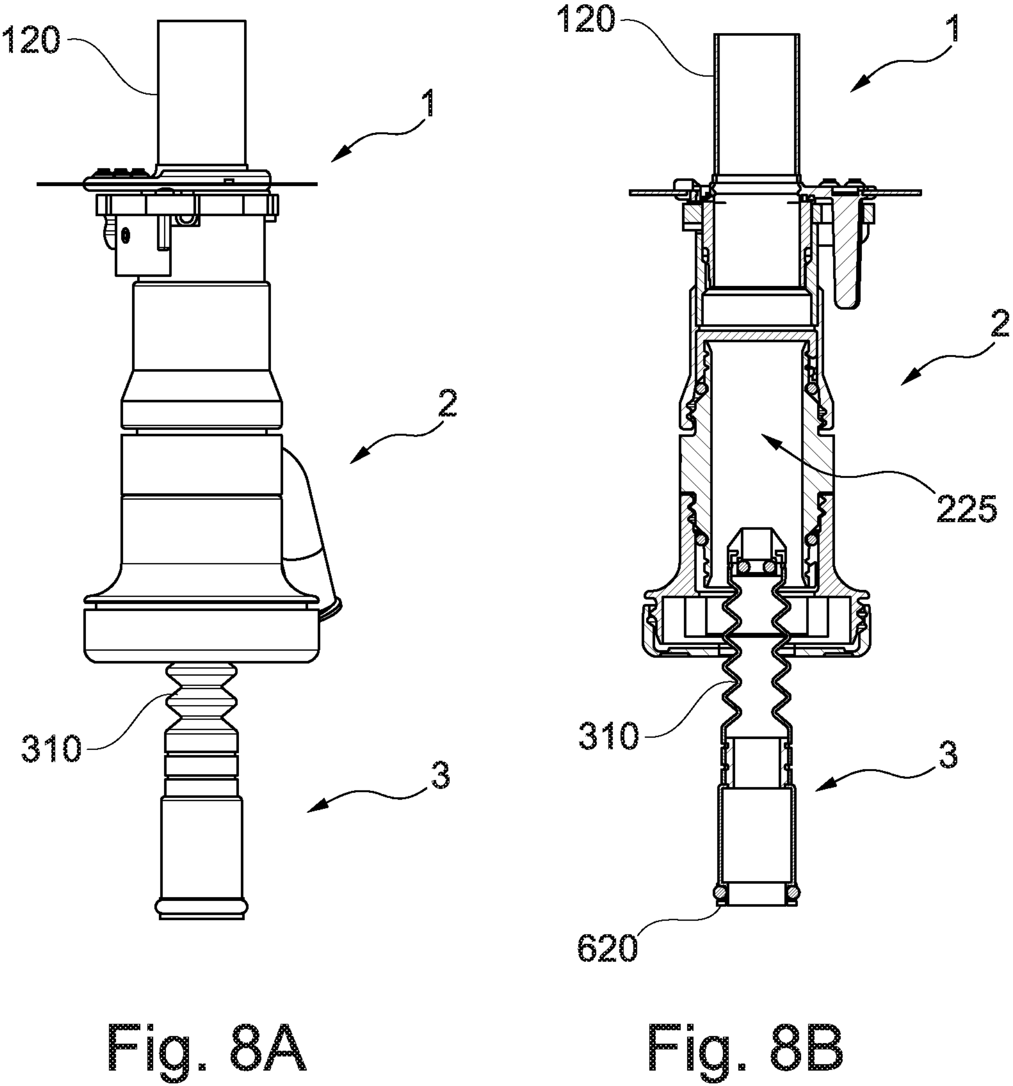
FIGS. 8A-B and 9A-B illustrate a transition from a first configuration to a second configuration of an access device 1.
Figure 9A:
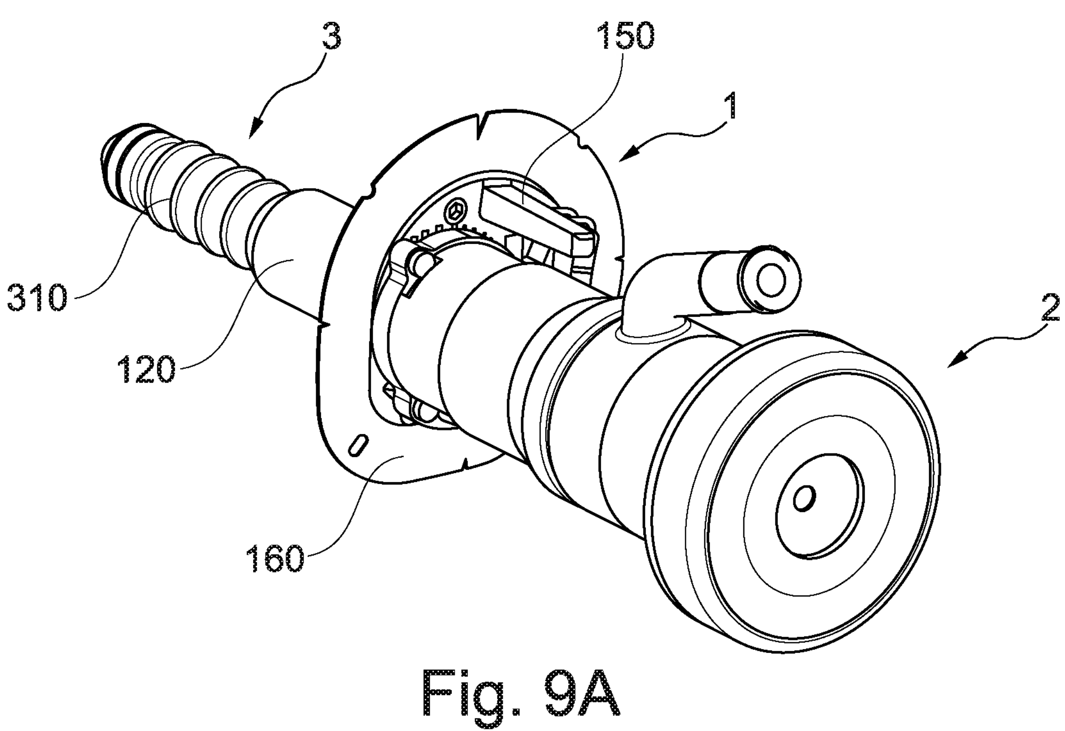
Figure 9B:
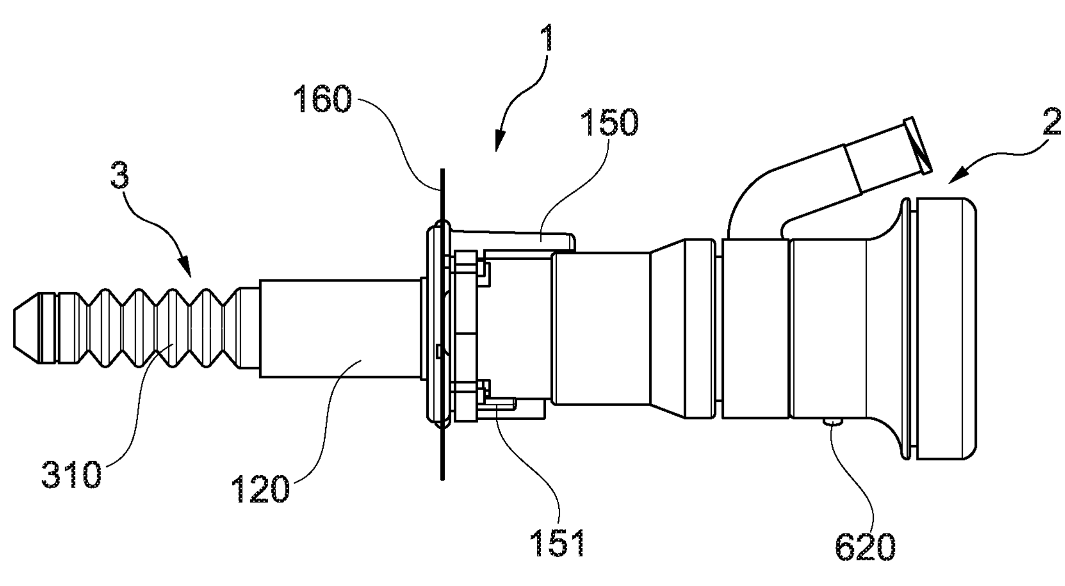

The second configuration of the access device 1 is provided as an alternative or in addition to the first configuration thereof. The second configuration of the access device 1 may be provided in addition to the first configuration during a transition from the first configuration to the second configuration only, e.g. when the sealing unit 3 is delivered to the apical base plate 100 through the hemostatic valve unit attached to the apical base plate 100. This has the advantage of avoiding blood leakage when changing configuration of the access device 1. A transition from the first to the second configuration is illustrated for instance in FIGS. 8A and 8B. A co-existent first and second configuration is illustrated for instance in FIGS. 9A and 9B.

As can be seen in FIGS. 8A and 8B and 9A and 9B, the sealing unit 3 of the access system is in examples configured to be delivered through the hemostatic valve unit 2 for a transition from the first configuration to the second configuration. In the second configuration, the separation is provided between the wet zone and the dry zone.

The hemostatic valve unit 2 may include one or more units to control the opening cross-section or aperture of a port 210 of the valve. These one or more units to control the aperture may, like housing 200, be splittable for instance for peel-on and/or peel-off of the units as described herein. Splittable is preferably provided by a construction of at least two parts joined together to form one unit. For instance, mechanical, or magnetic, preferably releasable joints may be provided for the joints. In particular, as illustrated in the Figures, the housing parts are preferably splittable in an axial/longitudinal direction of the valve unit 2. In this manner, the housing parts are preferably removable radially outwards, herein called "peel-off" operation. Other unit(s) may then be providing sealing of the wet dry zone of the apical base plate, such as the bellows described herein. Re-assembly may be made in a reverse radially inward assembly of such housing parts of a valve unit 2, herein also called "peel-on" operation.

Such unit may move or size suitably for such control. Examples of units include inflatable balloons, leaflets (moveable or fixed), and/or flaps (moveable or fixed). The aperture may be controlled by units similar to camera lens aperture diaphragms or iris like units. The units may alternatively or additionally include directional flow control elements, such as valves. The controlled directional flow may be uni-directional, i.e. in one direction only, or bi-directional, i.e. in two directions (forward, backward flow).

FIGS. 3A and 3B illustrate a hemostatic valve unit 2 while FIGS. 4A and 4B illustrate example of two different inflatable balloon configurations of hemostatic valve units 2. The removable hemostatic valve is connectable to the through port 120, i.e. a fluid communication channel is provided through the hemostatic valve to the through channel 120. The hemostatic valve 2 may for instance include one or more sealing elements (not shown) suitably arranged against the access device 1. For instance, such sealing elements may be provided as pressing against the apical base plate proximal side and/or a proximal end portion of the tubular through port 120.

The hemostatic valve unit 2 includes a housing 200 with approximal end and a distal end. The housing 200 may be splittable for instance for peel-on and/or peel-off of the hemostatic valve unit 2 as described herein. The distal end is affixable to the access device 1. The ends include an opening for access to a through channel of the valve 2. The though channel includes an inflatable balloon, via an inflation port 210. The inflation pressure provides a more or less restricted passage through the through channel of valve 2, i.e. the orifice of the valve through port 225 is variable by the inflation pressure (as illustrated by the double headed arrow in FIG. 4A). Devices inserted through the through channel may have varying diameter or cross-sectional shape, wherein the balloon pressure is adapted to this cross section to provide a reliable sealing. In this manner, the through channel of valve 2 accommodates a large range of devices diameters and cross-sectional shapes. As shown in FIG. 4B, the balloon 220 may have multiple lobes to further improve the adaptability to and range of different diameters or cross-sectional shapes of devices accommodatable for passage through the through channel of the valve 2 while safely providing reliable sealing and leakage protection of blood from the interior of the heart to the outside of the heart.

The hemostatic valve unit 2 is illustrated removably affixed to an access device 1 for instance in FIGS. 5, 6, 8, and 9. A sealing surface 230 is provided for fluid tight sealing against a sealing surface 130 of access device 1, such as at the apical base plate 100. The sealing may include a sealing member, such as an O-ring for improved sealing.

The hemostatic valve can for instance be reliably removably affixed to an access device's 1 via a bayonet joint 155 including bayonet pins 255.

As shown in FIGS. 25A, 25B, 25C, 25D, and 25E, the housing 200 of valve 2 is in examples splittable, with 202, 204 splittable housing parts of the valve 2 as mentioned above. In this manner, the valve 2 can be disassembled from parts that are positioned in its through port 225. Blood leakage may effectively be prevented by other parts, e.g. as shown in FIG. 24A. An access device 1 with affixed sealing unit 3 provides bleeding prevention as described above. With a medical device having a larger proximal diameter than the through port 225, the valve 2 cannot be withdrawn proximally for removal from the aggregate. There can be mechanical obstacles preventing that the valve 2 is retracted. For instance, a drive unit 6 may be affixed proximally to the aggregate of access device 1 and sealing unit 3 as shown in FIG. 24A. The splittable valve 2 may then advantageously removed from the aggregate upon assembly of the other parts by deflating the balloon 220 and splitting the valve 2. The valve 2 is arranged to be peeled off. The split parts of valve 2 can then be removed from the patient as valve 2 is no longer needed. Alternatively, or in addition, the splittable valve 2 may be opened only while parts still are connected to each other. For instance, two adjoining parts of a splittable valve with several parts may be separated from each other for opening the splittable valve 2, while still having part being adjoined, e.g. by a hinge, splint, string, or similar joint (like an open ring). Alternatively, or in addition, the valve 2 can be subsequently re-assembled and for instance re-attached to an apical base plate as desired (e.g. peel-on), either during the same procedure or at a later time after adequate sterilization.

Examples for peel-on and peel-off of a hemostatic valve 2 may be applied in reverse for each of these operations, respectively.

A valve 2 may later be re-attached, for instance to a configuration as shown in FIG. 24A if sealing is desired again, e.g. for repair or replacement of components of the aggregate or other parts of the system. The access device 1 thus provides for a re-access to the inside of the heart 15 at a later point in time.

The access device 1 may comprise a drive unit 6 of a cardiac assist device connected to the base plate in the second configuration. A rod 610 (FIG. 11A and FIG. 23) may transfer a movement generated by the drive unit into the heart chamber for cardiac assist. The distal end of the rod 610 may be connected to an anchor at a heart valve region, like anchor unit 650 in the example of an annuloplasty implant.

An anchor unit in the form of an annuloplasty implant is described in unpublished PCT application of the same applicant with PCT application number PCT/EP2019/068597 filed 10 Jul. 2019, which is incorporated herein by reference in its entirety for all purposes, but in particular the description of the chain annuloplasty ring and delivery system shown in FIGS. 24 to 42 and the corresponding description.

Coupling of the rod may be made magnetically, e.g. with a sealing unit 3 shown in FIGS. 24A, 24B and 24C. A magnetic coupling 340 at the distal end of the sealing unit may provide advantageous coupling with a firm link at the coupling point that allows for rotational movement and adaptation of the movement. A hollow in the magnetic coupling may be provided as a hollow funnel for receiving a spherical ball coupling to allow for this movement and geometrical adaptation during assembly and operation of the assist unit. Such a magnetic clutch coupling provides a number of advantages, for instance an overload protection. The magnetic connection can be configured such that it uncouples at pre-defined threshold forces to avoid tissue damage. The uncoupling possibility of the magnetic clutch coupling also allows for easy repair of components of an assist system, e.g. for repair, replacement or removal thereof.

Coupling means are described in unpublished PCT application of the same applicant with PCT application number PCT/EP2019/068595 filed 10 Jul. 2019, which is incorporated herein by reference in its entirety for all purposes, but in particular the description of the coupling unit 200 and extension units 400, including magnetic and linked joint couplings as for instance shown in FIGS. 5 and 6 thereof as well as the corresponding description.

In FIGS. 7, 8, 9, 10, 11, 22, 23 and 24 examples of sealing unit 3 are illustrated in various configurations.

The sealing unit includes in examples a membrane or bellow 310 and a feed through port 320. The feed through port may be completely sealed with no through going opening, such as for magnetic couplings. Alternatively, or in addition, a feed through port may have a distal opening for feeding through an element like a rod 610. The distal opening is then provided with a sealing member 326, such as an O-ring, for sealing the feed through port and providing the separation of the wet zone and the dry zone while allowing for a movement transferred between the zones. The sealing unit thus allows for instance reciprocal movement, e.g. in a cardiac assist/driving unit arrangement for safe reciprocal movement over millions of repeated cycles without leakage.

The membrane or bellows is preferably in examples made of an elastic and/or flexible material, such as silicone or the like. Bellows may be made of metal material like biocompatible metal materials such as Titanium or Nitinol. The bellows is movable in a longitudinal direction, e.g. for reciprocal cyclic movements. It is also moveable radially allowing for free motion or rotation as described herein. In examples, the bellows is rotating simultaneously as the bellows moves in operation in a longitudinal direction. In this way, there will be a rotation of a bellows upon forward and backward reciprocal movement, causing the bellows to have a type of threaded motion or corkscrew like motion. This combined motion is for instance providable by such elastic and/or flexible material of the bellows. A bellows which allows for rotation may have beneficial features since it would mimic the natural muscle contraction causing a helix heart movement. Such advantage features may e.g. be lower friction of the bellows. Other advantage features may e.g. be less stress and tension on the bellows causing a longer lifetime of the bellows.

In case the through channel is desired to be closed, this may be done by means of a plug (not shown) insertable into the through port 120.

FIGS. 3, 4, 5, 6, 8, 9, 19, 20, 21, 24 and 25 illustrate example of a hemostatic valve unit 2 in various configurations.

A hemostatic valve unit 2 has a housing 200 with a distal end and a proximal end. It is removably connectable at the distal end thereof to an apical base plate 100 of an access device 1 for a heart 10. The valve unit 2 includes a pneumatic valve in a through channel 225 of the valve unit 2 between the distal end and the proximal end thereof.

The pneumatic valve is for instance a balloon valve or a tube coil for controlling an inner passage in a through channel of the valve. A balloon valve has generally a larger range than a tube coil, which in turn can be provided with reduced height of the valve. A balloon valve is schematically shown in FIG. 4, while the valve shown in FIG. 25 may have a tube coil, for controlling the passage in the through channel.

The housing 200 has a proximal end with an opening to the through port 225 of the valve unit 2, such as for receiving a medical device to be passed through the inner passage of the valve unit 2.

The hemostatic valve unit 2 can in examples include a pneumatic reservoir unit (not shown) for maintaining a substantially constant pressure on the pneumatic valve.

In some examples the housing 200 is splittable. It has for instance multiple splittable housing parts 202, 204. As shown in FIG. 25. This allows for the herein described advantageous peel off when the valve is split.

The valve unit 2 may be re-usable.

In FIG. 4A a single lobe "donut" balloon is illustrated.

In FIG. 4B a balloon with multiple lobes 222 is illustrated.

An inflation port 210 is connectable to a pressure regulation source for controlling the pressure in the balloon. Various pressures provide for various expansions of the balloon, and also for varied pressure on devices introduced into the through port 225 and in apposition to the balloon's exterior wall. Sealing is thus secured over a wide range of cross sections of devices to be entered through the port 225. For instance, a small needle or comparatively large tube can be entered through the valve without bleeding.

In FIG. 5, the valve 2 is illustrated attached to an access device 1. This assembly is illustrated in FIG. 6 being attached to the heart 10 creating a transapical access to a heart chamber.

Figure 19A:
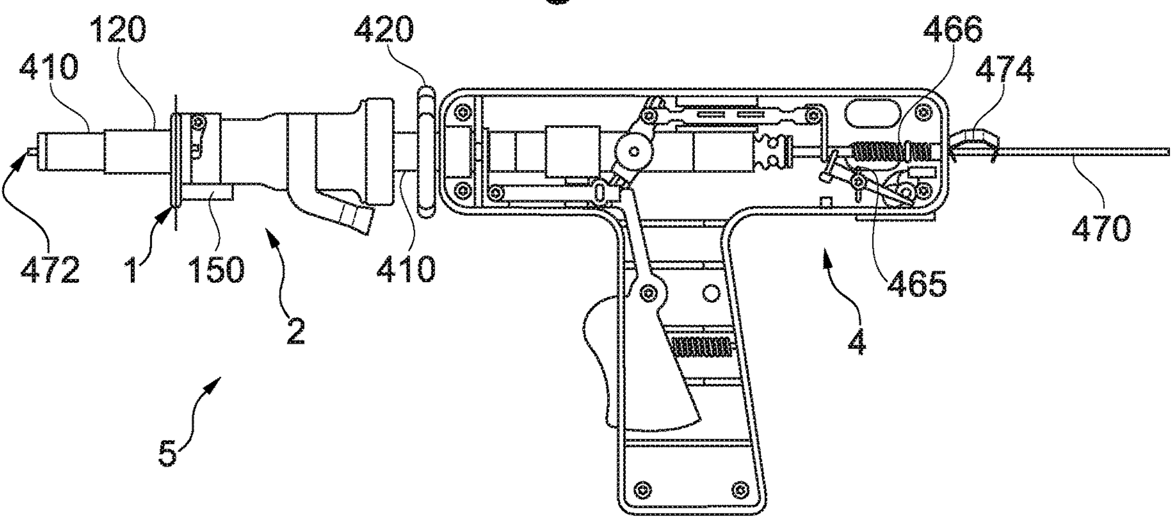
FIGS. 19A-B illustrate an example of a transapical access system 5 assembled and ready for use including an applicator tool, an access device for a heart and a hemostatic valve.
Figures 20A, 20B:
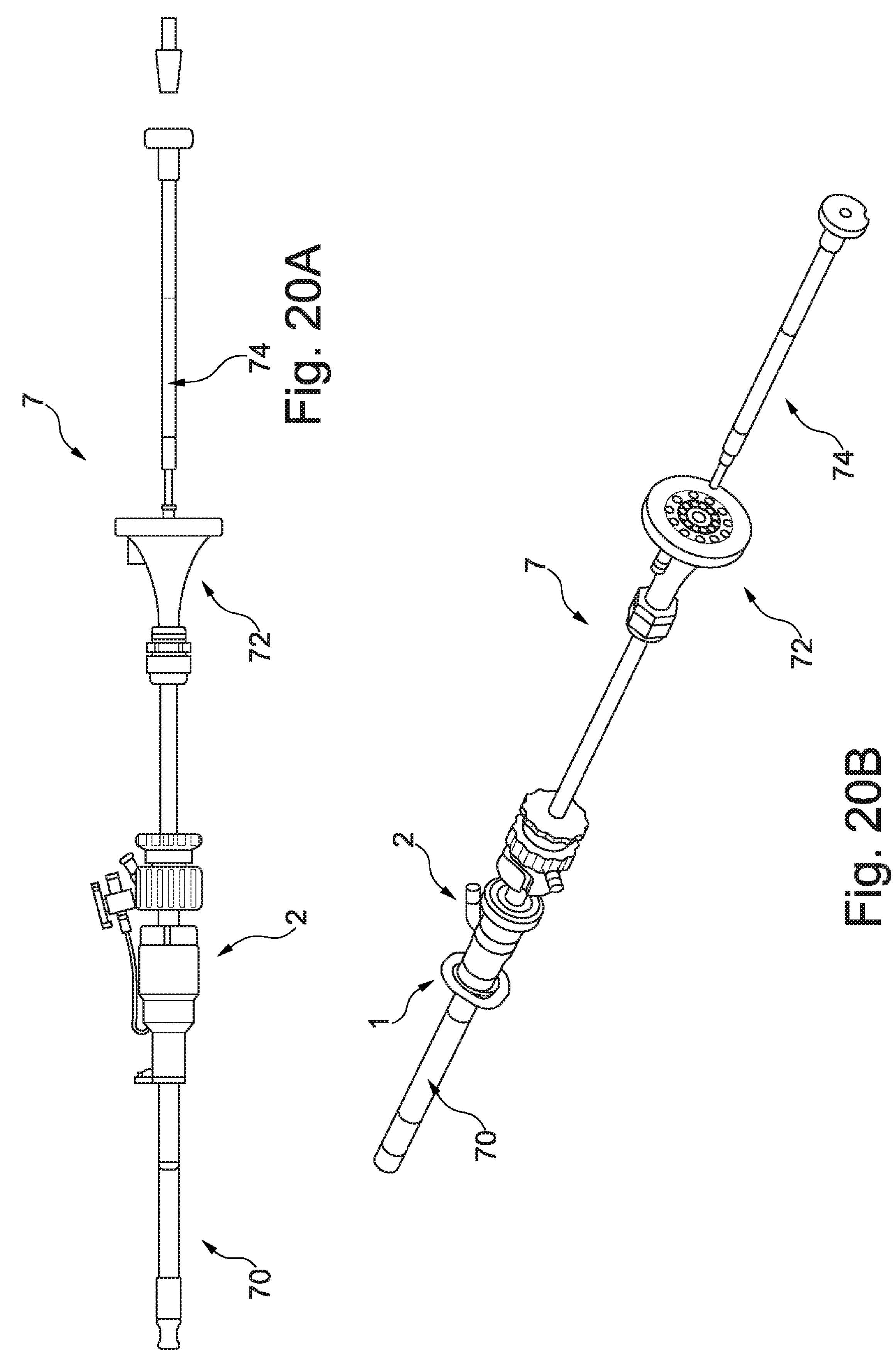
FIGS. 20A-B illustrate a delivery device for a medical device to the interior of the heart, insertable through a hemostatic valve and an access device in a first configuration.
Figure 21:
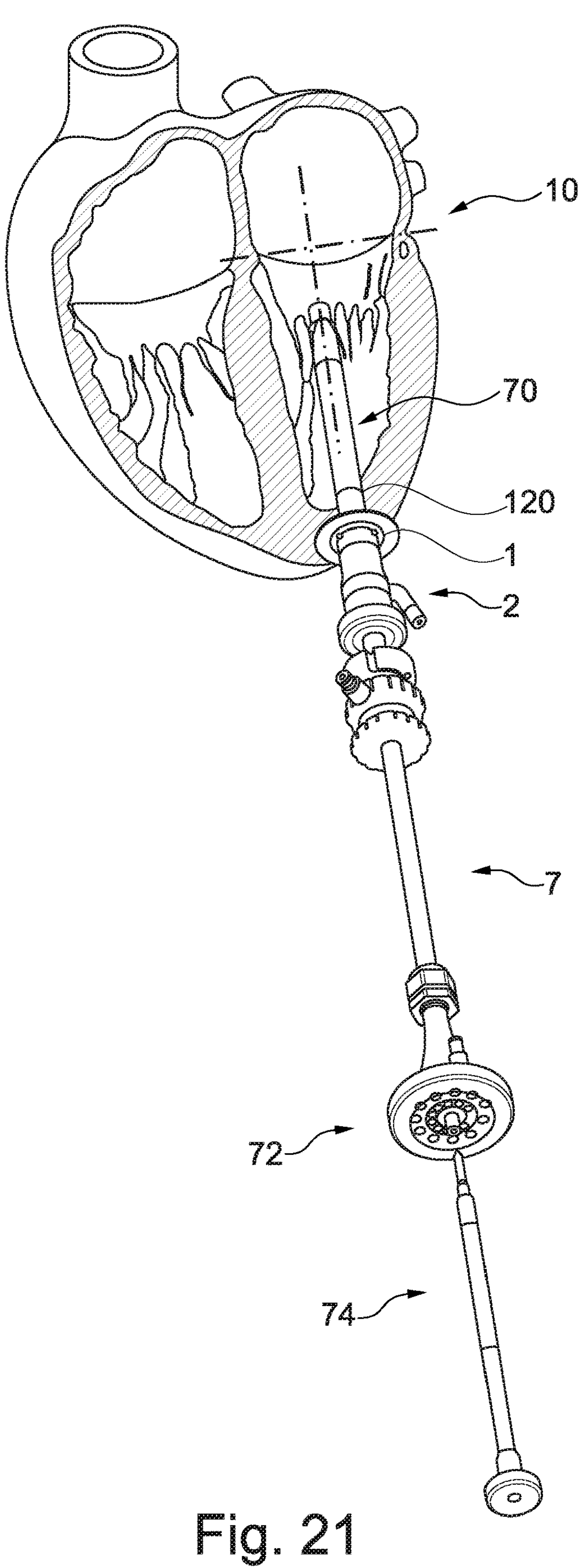
FIG. 21 illustrates the delivery device of FIGS. 20A-B transapically inserted into a heart through a hemostatic valve and an apical access device in a first configuration as described herein.

In FIGS. 19A and B, the hemostatic valve 2 is illustrated attached to the applicator tool 4 over the tube 410, and in FIGS. 20A and B attached to a delivery system 7 for delivering medical devices into the heart, as illustrated in FIG. 21. A delivery tube 70 of the delivery system is configured to be inserted into the heart chamber 20. The delivery tube 70 is in the example shown inserted through the access device 1 with attached valve 2 (see FIG. 6). The distal end of the delivery tube 70 is in the example advanced through the left ventricular chamber towards the left atrial chamber. A pusher 74 may be used to advance medical devices or other medical system assembly components through the delivery tube 70 to the inner of the heart. The delivery system may include a funnel shaped inserter unit 72 for facilitating insertion of such devices and components into the proximal end of the delivery tube 70. For instance, an anchor unit 650 may be delivered through the delivery tube 70 to the cardiac valve area as illustrated in FIG. 21 (at distal end of delivery tube 70) and in FIG. 23 (delivered and attached to valve area and also a rod 610). The anchor unit is for instance the annuloplasty chain implant mentioned above and described in PCT application number PCT/EP2019/068597, and in particular the chain annuloplasty ring and its delivery system shown in FIGS. 24 to 42 and the corresponding description therein. A chain annuloplasty ring may be affixed to a cardiac annulus, like the mitral valve annulus as illustrated, by means of multiple anchor screws (not shown). These screws may be rotated into the annulus tissue by suitably attached screwdrivers (not shown) having proximal ends accessible for rotation passed through a lock of the inserter unit 72.

Once, the anchor unit 650 is installed, a driving rod 610 can be attached to the anchor unit 650 via the access device 1. The rod 610 may for instance be pre-installed through a sealing units' 3 feed-through port 320 and installed together into the access device 1 through a hemostatic valve 2 as described herein. The rod 610 may also be installed first and then the sealing unit 3 is then installed with its bellows over the rod 610 through the valve 2. The valve 2 can then be removed while drive unit 6 becomes connected to the driving rod 610 and access device 1, leaving a wet dry zone separation implanted in the patient with the cardiac assist system installed.

In FIGS. 12-19 examples of applicator tools 4 for advantageously creating a transapical passage on a beating heart are illustrated, for instance with a tube 410 that has a sharpened edge at a distal end thereof.

The applicator tool includes in examples a harpoon 450 insertable through a tube of the applicator tool. The harpoon 450 includes a rod member 470 that is housed inside a hollow penetration needle 460 that has a distal tip for penetrating cardiac tissue at an apex of a heart. The rod 470 member is preferably a solid rod with an expandable retention member 473 at the distal end 472 of the rod. The rod 470 is arranged longitudinally movable in the penetration needle. The penetration needle is inserted into the tube 410 and arranged longitudinally movable in the tube 410. The rod is preferably kept longitudinally stationary with the penetration needle 460 when it is longitudinally moved. The tube 410 has preferably a sharpened edge at a distal end for cutting the cardiac tissue at the apex.

In a first step, tube 410 is brought with its distal end into apposition at the desired location of the apex. The penetration needle 460 may be pushed at that location, such as determined with template 190, out of the tube 410 through the cardiac tissue to the chamber. The needle has a small enough diameter that substantially no bleeding occurs across the cardiac tissue at the puncture site. The harpoon 450 is stored in the penetration needle with expandable flanges in a collapsed configuration within the needle lumen and proximal to the sharp tip thereof, see FIG. 13A The distal end of the tube 410 may be brought into apposition at the desired apex region and then the penetration needle may be pushed through the apex. For instance, the penetration needle may be releasably activated by a trigger 465. The trigger releases the needle and it is pushed forward by a spring 466 released by the trigger 465. The needle is "shot" through the cardiac tissue in a quick and reliable manner.

Figure 15:
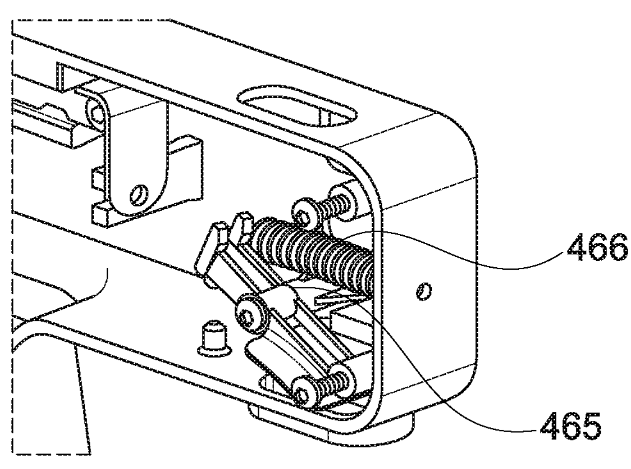
FIGS. 15 and 16 illustrate a detail of the applicator tool.
Figure 16:
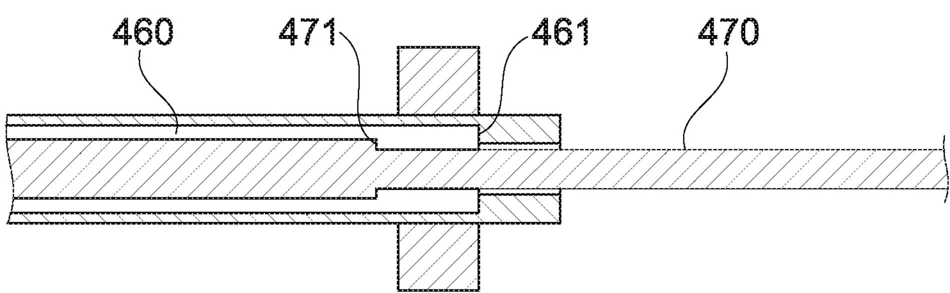
Figure 17:
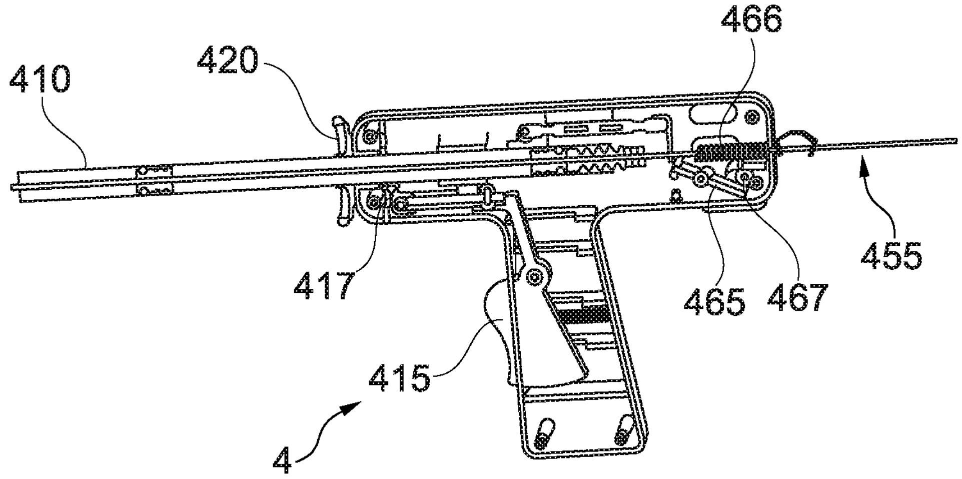
FIG. 17 illustrates the applicator tool in a configuration where the transapical puncture is made and a tissue plug is safely contained in the tube of the tool.

FIGS. 15 and 16 illustrate a detail of the applicator tool 4. More precisely, the proximal end portion of the penetration needle 460 housing the proximal portion of the rod 470 are shown. The rod 470 has a shoulder 471 such that the rod can be longitudinally moved relative the penetration needle 460. The shoulder provides a stop in the proximal direction, such that the relative position of the rod 470 to the penetration needle 460 in its retracted position is provided, see e.g. FIG. 13A for the distal end of the rod 470 retracted into the distal tip of the penetration needle 460. The seat 461 of the needle provides that upon triggering a forward push of the needle 460 and rod 470 aggregate can be shot together forward, e.g. by releasing the needle spring 466 in tension by activating the needle trigger 465, see e.g. FIG. 15, 17 or 19A and 19B. A safety pin 467 may be provided preventing unintended activation of the trigger 465. The rod 470 can then be moved in the distal direction with its distal end out of the penetration needle's 460 distal end for expanding the one or more retaining units 473.

Figures 13A, 13B, 13C, 13D:
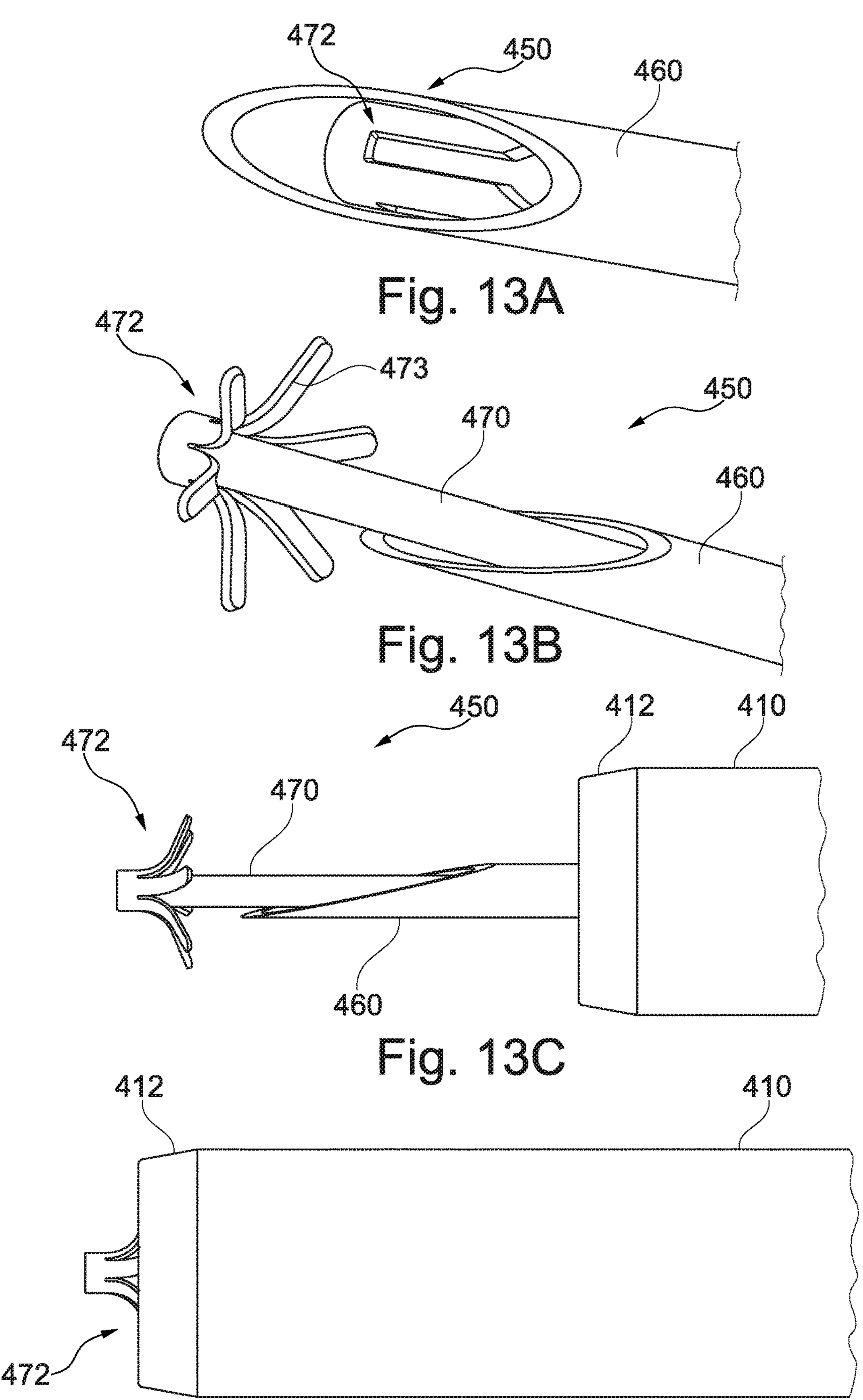
FIGS. 13A-D illustrate a harpoon needle, rod with a retaining unit in form of expandable barbs and a punch tube with sharp end edge assembly in different configurations.
Figure 18:
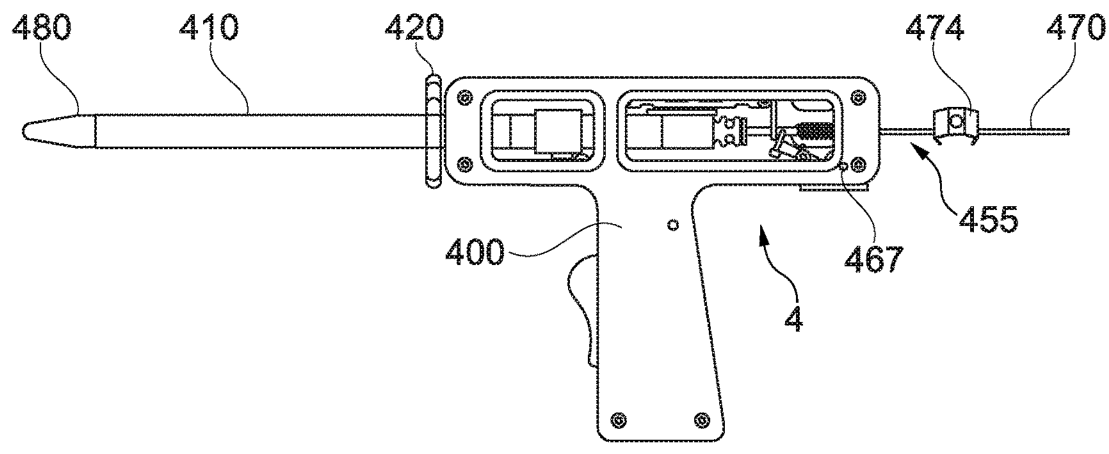
FIG. 18 illustrates an applicator tool with a dilator.

Thus, once the penetration needle is positioned through the cardiac tissue, the harpoon 450 may be pushed forward out of the penetration needle distal end. This may be done by pushing the proximal end 455 of the harpoon 450 in the distal direction while the penetration needle 460 is kept in position, for instance as described in the previous paragraph. The expandable flange is then expanded, e.g. by an elastic force thereof. The flange provides thus a retainer element for preventing withdrawal of the harpoon through the cardiac tissue, as illustrated in FIGS. 13B,C and 14B. A moveable and lockable stop element 474 may be provided for keeping the rod locked in position relative the grip 400 and/or tube 410, as illustrated in FIGS. 18 and 19A.

The harpoon with expanded retainer unit is then withdrawn towards the cardiac tissue, i.e. at the inner wall of the heart chamber. The shoulder 471 at the proximal end portion of rod 470 and expanded retaining unit 473 are abutting against the penetration needle. In this manner, the aggregate rod 470 and penetration needle 460 can be withdrawn proximally as a unit, e.g. by manually drawing the proximal end 455 in the proximal direction.

Figures 14A, 14B, 14C:
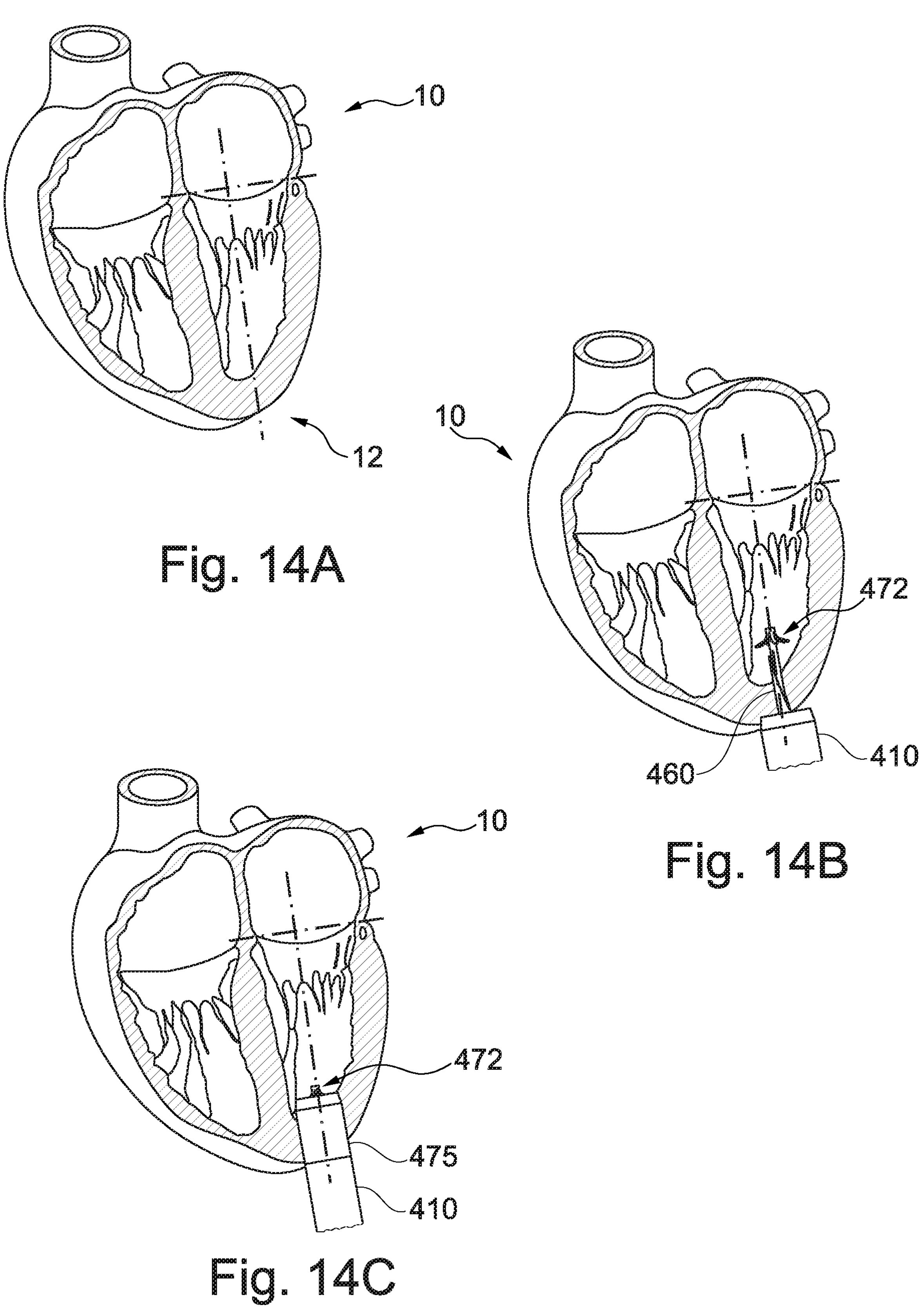
FIGS. 14A-C illustrate creation of a transapical puncture in a heart with an applicator tool shown in FIGS. 12 and 13.

The tube 410 is then pushed forward towards the retainer unit through the cardiac tissue, wherein the flange is configured to keep the cut cardiac tissue within the tube 410, as illustrated in FIGS. 13D and 14C. Tube 410 is arranged longitudinally moveable and is for instance pushed forward by using the trigger 415 in a safe and reproducible manner. The trigger 415 may be arranged to articulate a claw 417 that pushes the tube 410 when the trigger is activated accordingly. When pushing the trigger, the claw tilt slightly against the outside of the tube 410 and locks in place for the pushing action. Releasing the trigger 415 removes the tilting of the claw 417 which then can slide back over the tube 410 for the next forward trigger movement. This provides for precise activation of the movement with a compact mechanism. The cut cardiac tissue from the transapical hole thus created is safely kept inside the tube 410, as schematically illustrated in FIG. 14C as a tissue plug 475.

The tube 410 may be pushed forward, e.g. by operation of a trigger 415 of the grip 400. The tube may be suspended freely rotatable around its central axis. Cutting may be facilitated by rotation of the tube when moving through the cardiac tissue. Rotation of the tube may be provided by a control dial 420. In this manner, a quick, precise and efficient transapical hole is made. This is done with improved patient safety as embolization of cut cardiac tissue is prevented. The tissue that is cut is safely kept in the tube 410 with the harpoon flanges holding back the tissue in the tube, as illustrated in FIG. 13D. Complications like stroke are minimized or avoided by such examples of applicator tools for creating a transapical passage on a beating heart, which is a particular challenge because of the heart movements and related difficulties to contain cut tissue and prevent it from being entrained with the blood flow of the beating heart for instance.

The tube 410 has an outer diameter thus substantially corresponding to the diameter of the punched transapical hole in the cardiac tissue. In case a tubular through port 120 is installed in the transapical hole via said tube 410, the through port 120 outer diameter is slightly larger than the diameter of the transapical hole. Tissue around the transapical hole may thus elastically flex towards the outside of the through port's 120 tube and thus improve both ingrowth and sealing of the access device 1.

Figure 19B:
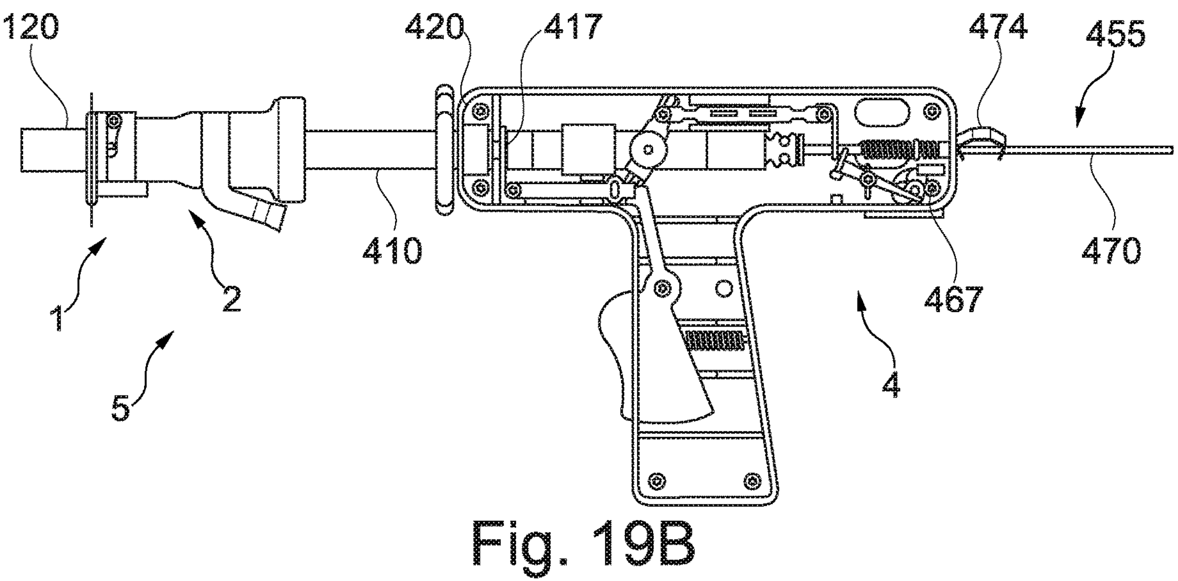

The distal end of the tube 410 is in examples in fluid communication with a proximal seal including a blood indicator 490. Blood entering the blood indicator via the tube 410 indicates penetration of the cardiac tissue into an interior/chamber 20 of the heart 10. As illustrated in FIGS. 19A and 19B, the applicator tool 4 can in examples also deliver a medical device. For instance, the device is arranged over the tube's 410 outside and can slide over the tube 410.

The medical device is arranged to be matingly received with an inner channel of the device slidable over the tube's 410 outside. It can for instance be slid onto the tube from the distal end thereof for assembly as shown in FIG. 19A. A conical protection unit may temporarily be put on the distal end orifice of the tube 410 for sliding the medical device onto the tube, for instance to cover a sharp edge 412 of the distal end of the tube 410.

In FIG. 19B the device is illustrated being slid forward.

In an example, the device incudes an apical access device 1. The device may include a hemostatic valve unit 2 removably pre-attached thereto.

The apical base plate can be slid forward over tube 410 and with its tubular through port 120 into the through hole, still with the distal end of tube inserted through the cardiac tissue. When the flange unit 160 is sealingly attached to the apex, the applicator tool can be withdrawn out of the port 120 and the valve unit 2. This leaves the aggregate of an access device with attached valve unit 2 in position as shown in FIG. 6.

The transapical port is then usable, e.g. for delivery of devices to the heart chamber or performing procedures as desired. Eventually the sealing unit 3 may then be installed for providing the wet/dry zone separation. A medical device like a driving unit of a cardiac assist device can be installed at the dry zone of the access device 1. The valve unit may be removed. The procedure can then be concluded, leaving a wet/dry zone separated device implanted in the closed patient body.

FIG. 18 illustrates an example of an applicator tool for creating a transapical passage that includes a penetration needle insertable through a co-axial dilator 480 of the tool. The penetration needle 460 has a distal tip for penetrating cardiac tissue at an apex of a heart.

This example does not include a harpoon. However, a tool 4 as described previously with a harpoon-based tissue retaining member and cutting tube may provide for preparation of a hole substantially lesser than a tubular through port 120 (not shown in the Figures). The diameter of the hole may then be widened by a dilator 480. The applicator tool 4 may furthermore include an access device for a heart that has a tubular through port to be arranged across the cardiac tissue when advanced over the dilator. Also, a removable hemostatic valve unit 2 may be included in examples of such a tool 4 attachable to the access device 1 and slidable over the dilator 480.

Hence, a transapical access system 5 for creating a transapical passage on a beating heart is provided. The system includes an access device for a heart according to the afore described aspect of the disclosure. In addition, the system includes an applicator tool for creating a transapical passage and delivering the access device to an apex of the heart, as described above according to the afore described aspects of the disclosure.

The system may include a fixture template 190 for targeted puncture of the apex. The fixture may be provided in examples with a patient specific shape for the apex of a particular patient's heart 10. The specific shape may be selected from multiple pre-manufactured fixtures of different shapes. The template 190 may be manufactured with a specific shape based on imaging data of the apex, for instance CT based imaging data.

Figure 22A:
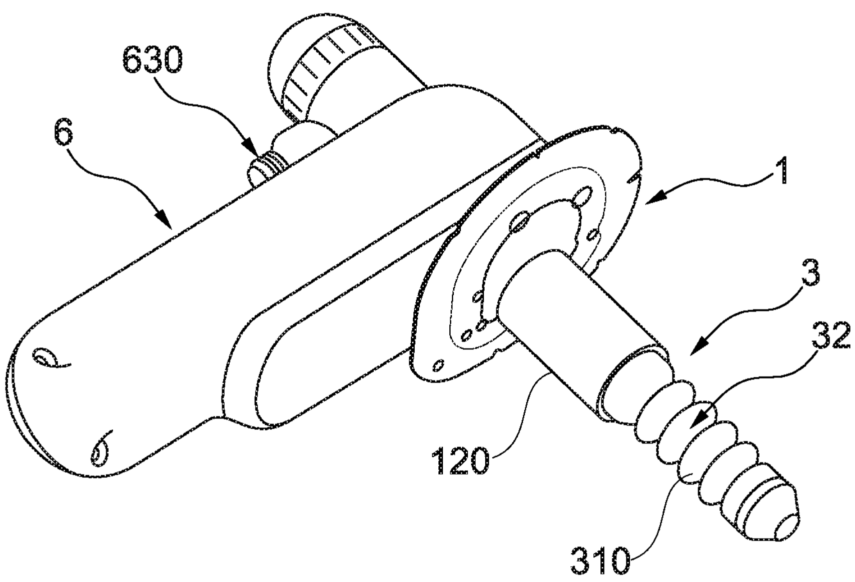
FIGS. 22A-B illustrate an example of a medical system including a cardiac assist unit to be transapically implanted attachable to a sealed apical base plate.
Figure 22B:
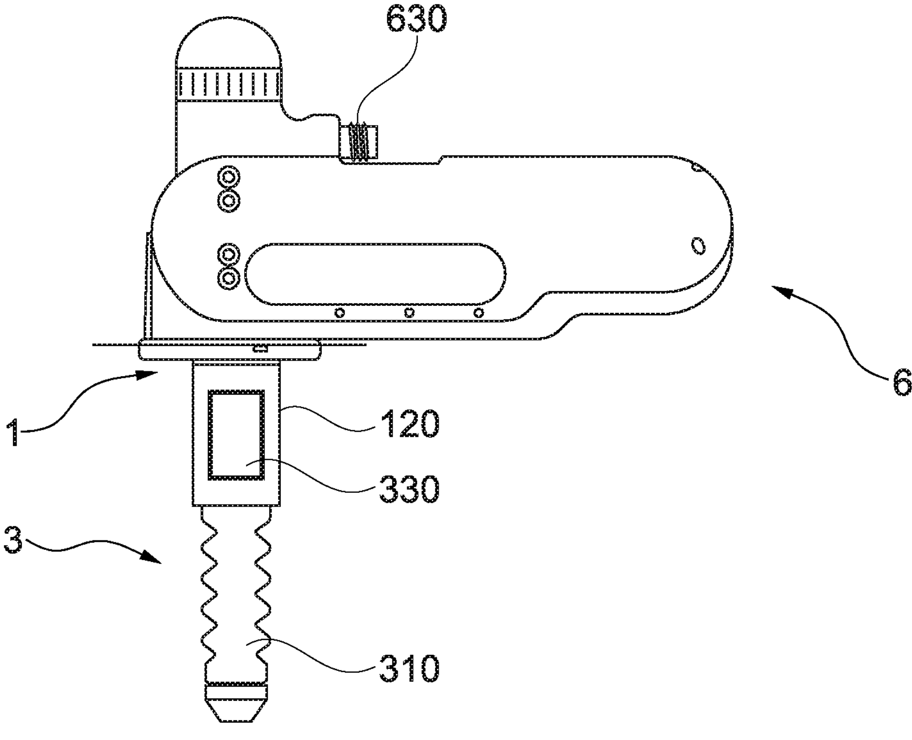
Figure 23:
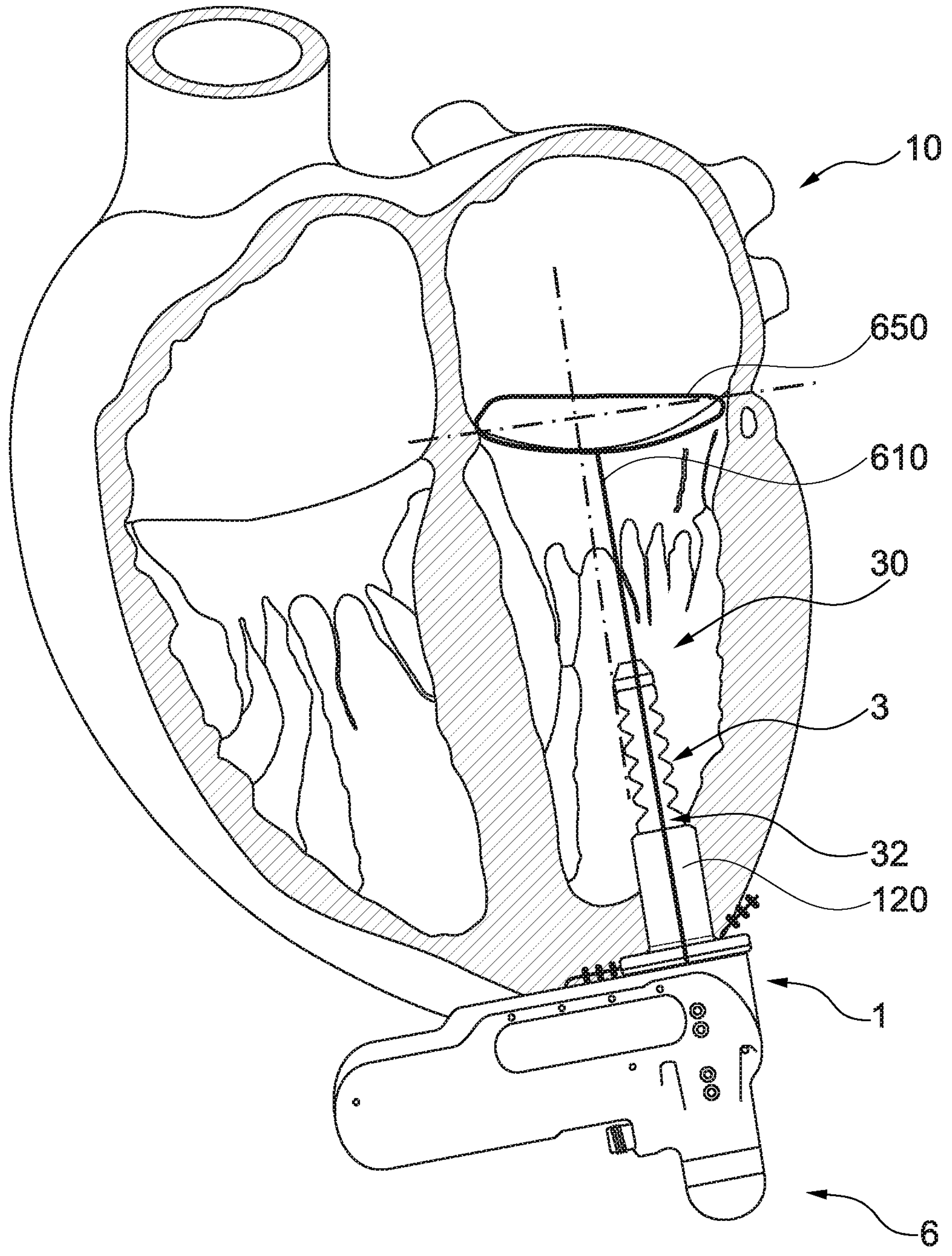
FIG. 23 illustrates an implanted access device with sealed apical base plate and attached cardiac assist unit.
Figure 25C:
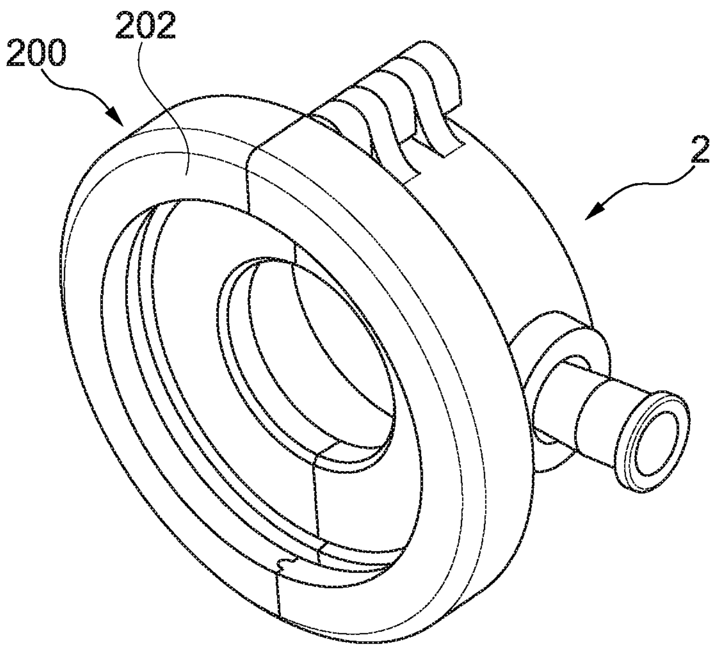
Figure 25D:
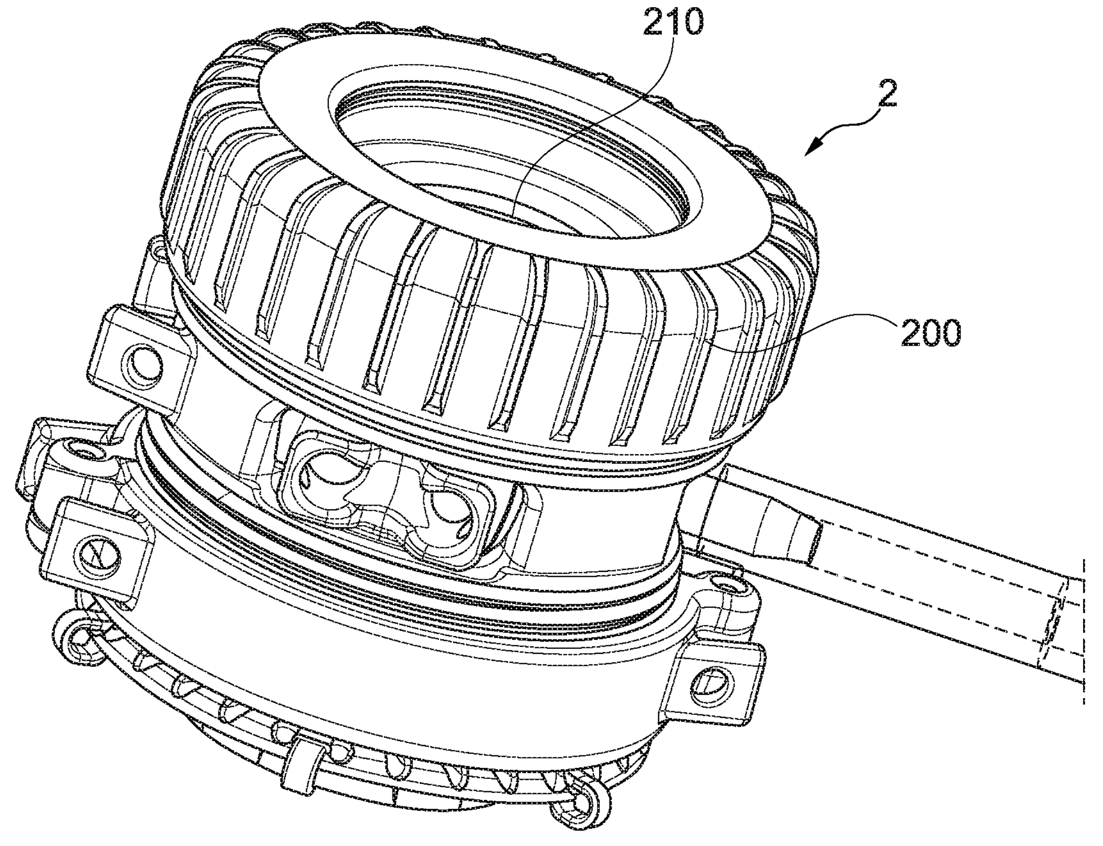

FIG. 23 illustrates an example of a medical system including a cardiac assist unit transapically implanted. A drive unit 6 of the cardiac assist unit is illustrated attached to a sealed apical base plate 1 which is implanted and providing a transapical passage with a wet/dry zone separation as described above. Hence, the mechanical and electronic parts in the drive unit are in a dry zone (inside its housing and inside the sealing unit 3). A driving rod 610 is attached to an anchor unit 650. In FIG. 22A, B and FIG. 23 the electronic parts in the drive unit may have a cable through-port for electrical connection 630 of a cable to e.g. an external cell, battery or other power supply. An illustration of such an electrical connection 630 is seen in FIGS. 22A, B and FIG. 23. Note that the tread shown at electrical connection 630 is optional or alternative for securely connecting a cable. The cable through-port typically ends up in an electrical connection for instance in the form of e.g. a Bal Seal connector like a "Bal Conn® Electrical Contact" or a "SYGNUS® implantable contact system" or similar connection systems, such as on top of the housing The access device 1 is in examples a cardiac anchor unit as part of an implantable medical device system. A cardiac anchor unit and cardiac assist principles are for instance disclosed in WO 2011/119101A1 of the same applicant that the present application, in particular in FIG. 11*c* thereof and related description regarding a left ventricle arrangement for assisting the mitral valve piston like movement. This document is incorporated herein by reference in its entirety, and in particular regarding FIG. 11*c*. The access device 1 provides a particular advantageous implementation of such a cardiac assist system. Access device 1 may also be used in cardiac assist systems involving other configurations than disclosed in WO 2011/119101A1.

If further anchor units are present at the heart, like shown in FIG. 23, a relative movement is providable by the driving unit, e.g. via the rod 610. The access device 1 when implanted at the apex may be regarded having a static position, and a second anchor, like the chain annuloplasty anchor mentioned above, may be moved in a push/pull movement, e.g. synchronized with the heart's ECG, intracardiac pressure, cardiac output flow, or the like, for assisting the heart's pump action and thus treatment of a patient.

Figure 11A:
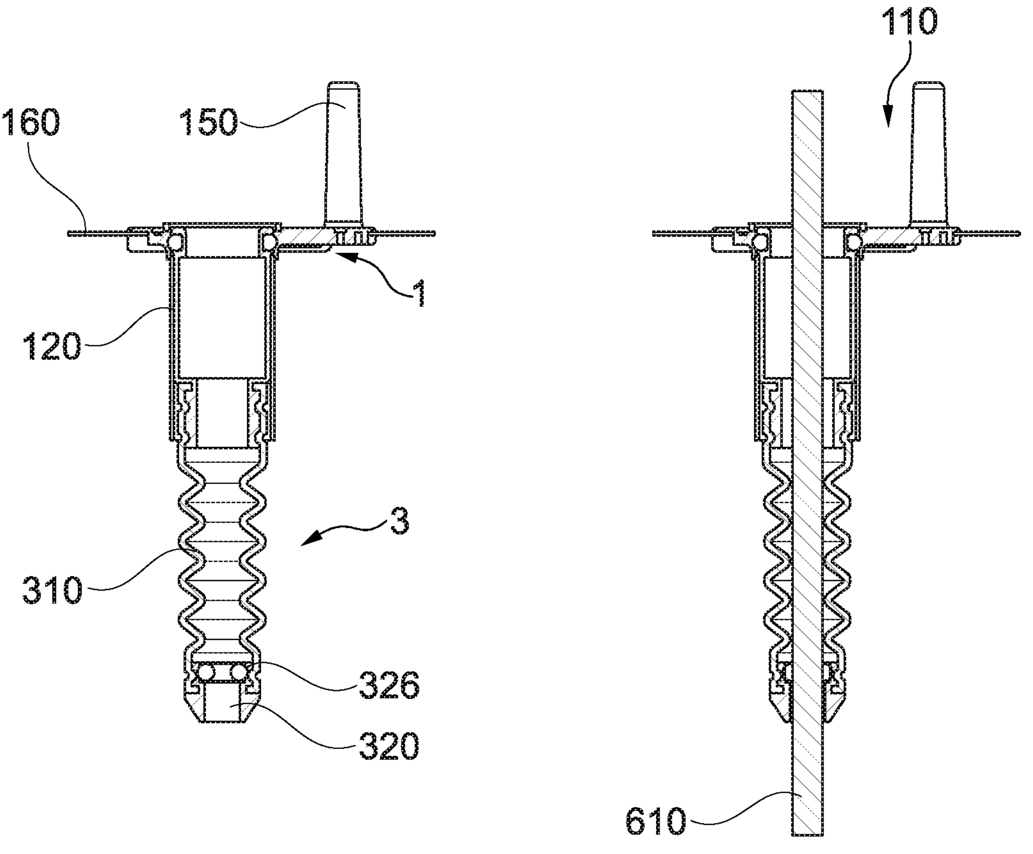
Figure 11B:
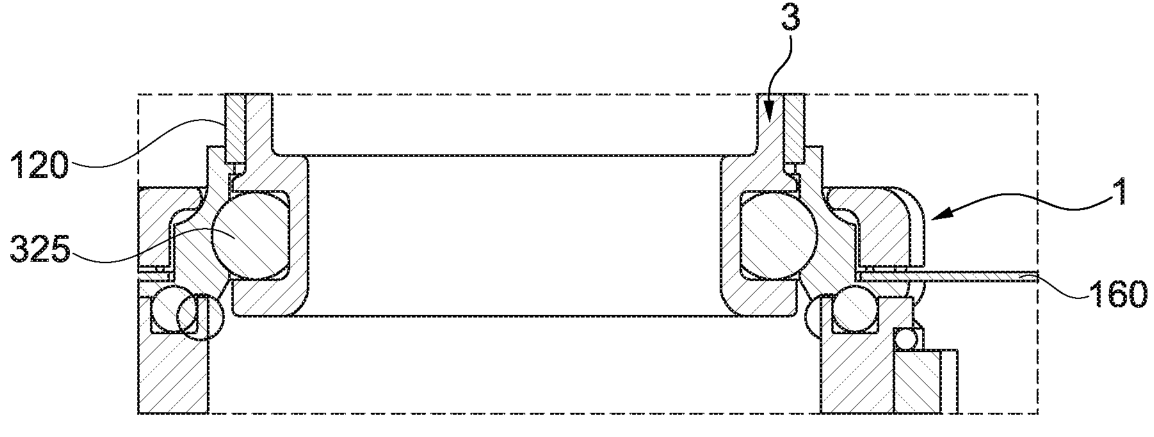
Figure 11C:
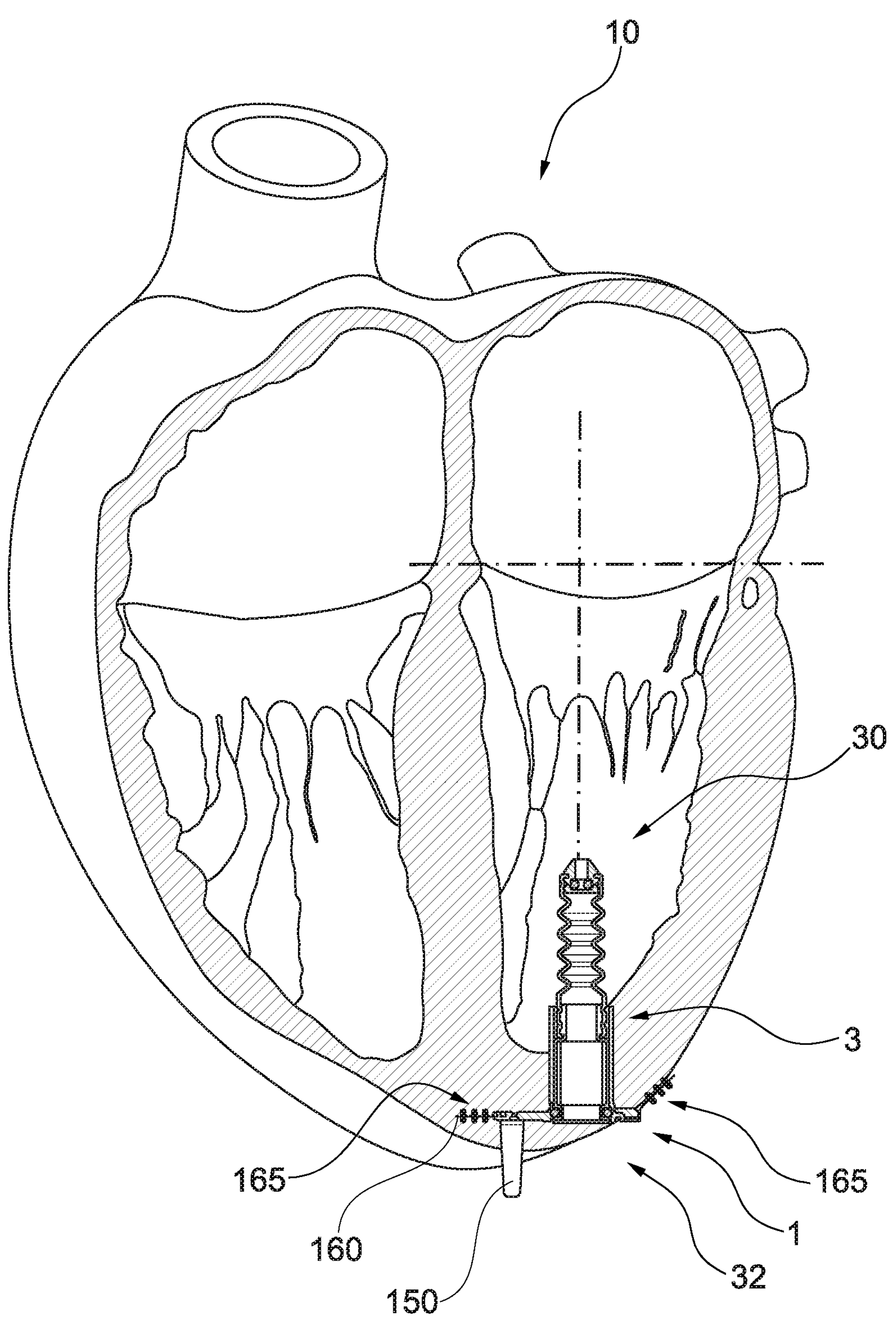
FIG. 11C illustrates an implanted access device in a second configuration.
Figure 12A:
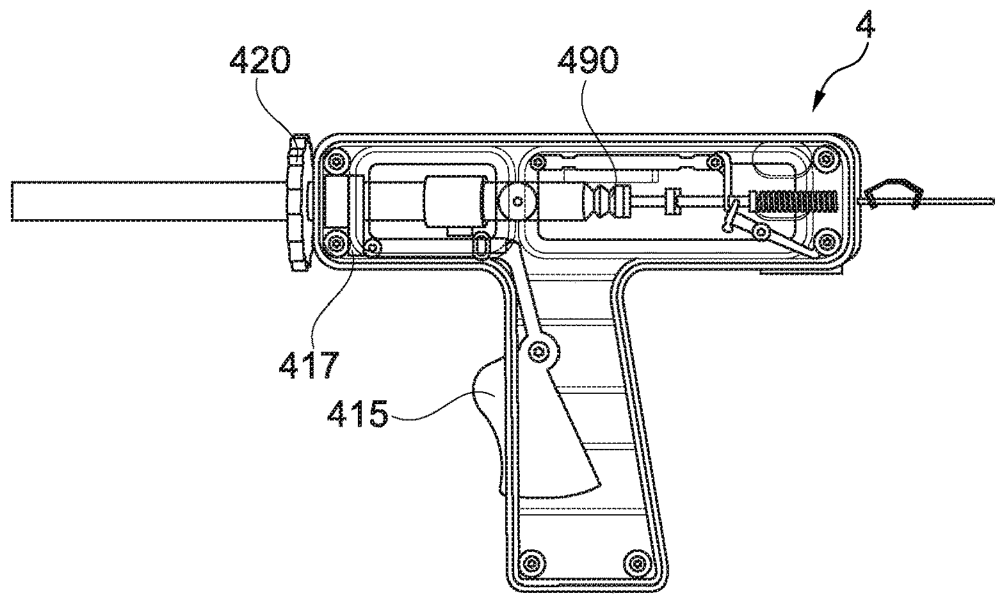
FIGS. 12A-B illustrate an example of an applicator tool for creating a transapical passage on a beating heart with a tube that for instance has a sharpened edge at an end thereof, while a grip with open lock is shown.
Figure 12B:
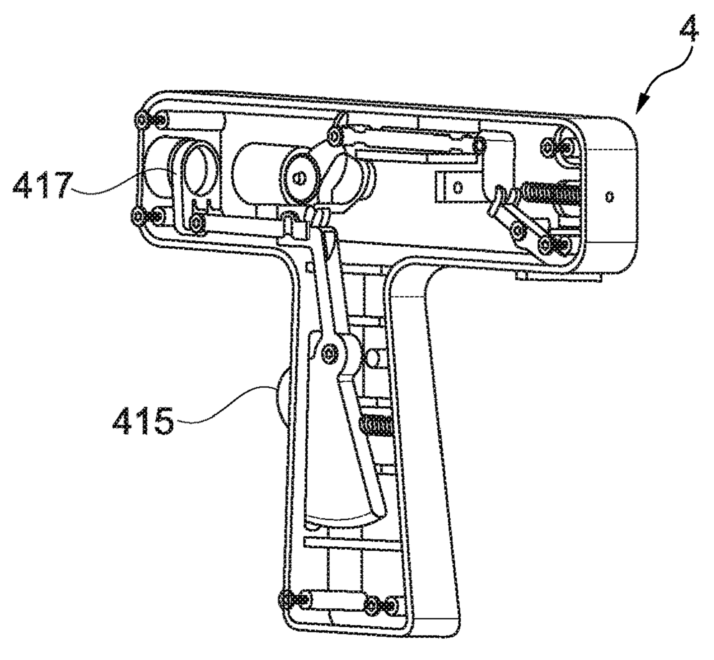

FIGS. 11A, 11B and 11C illustrate an example of a sealed apical base plate 1, which includes a connection interface 110 for matingly engagement of multiple medical devices. An example is the hemostatic valve 2 and the drive unit 6 that may be attached alternatively to the same connection interface. The multiple medical devices have in turn a mating connection interface designs for connection to the apical base plate, respectively.

In some examples, the connection interface is positioned on a proximal side of the apical base plate 1, and the apical base plate 1 is sealed on a distal side, opposite its proximal side.

The connection interface 110 may include a locking unit 115 in certain embodiments. The locking unit provides for secure mating engagement of the apical base plate 1 with such multiple medical devices when attached to each other. An example of a locking unit 115 is shown in FIG. 3A.

As is shown in the example of the apical base plate in FIGS. 28A, 28B, 28C, 28D and 28E, the apical base plate may comprise various connection interfaces 110 for mating with a medical device. In one example, a connection interface 110 may be an edge for e.g. matingly engagement with e.g. a locking clip. In another example the connection interface 110 may be a screwing hole e.g. for screwing in a screw, for example of M2 size, any suitable size may be used. In yet another example, the connection interface 110 may be a connection hole or a connection loop e.g. for matingly engagement with e.g. a suture, a wire, a thread, a fiber or similar. By way of example, FIG. 28F illustrates the apical base plate having two holders connected to one of the illustrated connection interfaces 110. It is to be noted that the apical base plate may comprise one or more connection interfaces 110. In some examples, more than one different connection interfaces 110 may be applied.

FIG. 26 illustrates steps of an example of a method 700 of creating a transapical passage on a beating heart.

The method or medical procedure includes determining a position 710 on an apex region for creating a transapical passage. This may for instance be done using an imaging modality providing suitable image data for processing and analysis, e.g. CT based, MR based, Ultrasonic based. Alternatively, or in addition, the position may be determined by tactile sensing and/or visual inspection of the heart, e.g. during surgery.

The method further includes creating a transapical hole 720 at the determined apex region through cardiac tissue, such as by punching and/or cutting through the tissue.

Creating the transapical hole may advantageously be performed using an applicator tool 4 as described above and illustrated in FIGS. 12 to 19. Creating the transapical hole may include penetrating cardiac tissue at the apex with a penetration needle 460 housing a distal tip of a harpoon 450 and through a tube 410. The forward penetration movement of the harpoon member and penetration needle 460 may be released by a trigger 465 so that these are "shot" forward as a unit in a one-shot movement, here through the apex wall. The one-shot movement is quick and reliable for making the initial puncture of the cardiac tissue.

When the harpoon is brought through the cardiac tissue, a rod member may be further advanced out of the penetration needle and one or more retention members may be expanded radially outwards from the rod's 470 distal end 472. The retention member is then withdrawn for apposition against the inner cardiac wall of the heart chamber at the puncture made by the puncture needle 460 (which is also suitably withdrawn into the puncture).

The sharpened edge 412 of the tube 410 is then pushed through the cardiac tissue towards the retention member. Pushing of the tube relative the rod member distal end 472 may be done by operating the trigger 415 of the pistol grip 400 in a safe and repeatedly standardized manner. In addition, a control dial 420 may be used by an operator for rotating the tube when cutting for improved cutting.

The expanded diameter of the retention member is preferably slightly smaller than the inner diameter of the tube 410 lumen so that the tissue plug can be completely withdrawn into the tube's 410 inner lumen, as illustrated in FIG. 13D. The retention member may also have a larger diameter. It may be brought into apposition with the sharp edge 412 of the tube 410. Thus, both retaining the tissue plug in the tube and covering the sharp edge, preventing potential unintended cutting by the edge 412 and increasing safety of the procedure both for patients and operators. In any case, embolization of the cut tissue plug from the apex is securely prevented.

The penetration of the cardiac tissue into the heart chamber an interior of the heart may be indicated to the operator with a blood indicator of the applicator tool 4. For instance, the blood indicator 490 may be provided at distal end of a tube of an applicator tool being in fluid communication with a proximal seal. The seal may include a transparent portion blood passing from the chamber into the distal end and the lumen of tube 410 passes through the tube 410 to its proximal end and indicates penetration of the cardiac tissue into an interior of the heart. The seal provides also for feed through of the penetration needle and rod member therein without leakage.

A dilator 480 may be used for widening the tissue hole created by the penetration needle 460 and/or the tube 410

The method further includes delivering 730 an access device, such as an apical base plate, which has a tubular through port to the transapical hole. Delivery may be made by sliding the access device distally over the outside of tube 410 and/or a dilator 480.

The method further includes attaching a flange unit of the access device to an outside of the heart. The flange unit may be attached around the transapical hole by a suture technique called "parachute technique". For the parachute procedure, both ends of a single suture 165 are sutured through the cardiac tissue around the hole at a suitable distance to the hole. This may be done using a suitable template for a number of sutures around the hole. For instance, 8 to 10 sutures around the periphery of the flange 160 may be sufficient for providing reliable seat of the access device in a sealed manner, i.e. without bleeding from the heart chamber when the channel in tube 120 is suitably closed by e.g. a hemostatic valve, sealing unit or a plug. The channel in tube 120 provides a transapical working channel to and from a heart chamber on a beating heart.

Bleeding is prevented by keeping the tube 410 in the hole. The two ends of each same suture are then passed through the flange unit, which is held away from the heart surface on the outside of the tube 410 of tool 4. The suturing pattern is repeated using additional sutures, resulting in several suture "pairs" spaced around the hole and tube 410. The access device 1 is then lowered or parachuted down against the outer heart wall and advanced until the plate 100 and the flange 160 are in contact with the heart surface and the opening of the tube 120 of the access device 1 is inside the heart chamber. After all the suture pairs are secured, e.g. by suitable knots, the result is a blood tight flange with a tubular port 120 in the transapical hole.

The method may further include removably connecting a hemostatic valve unit 2 to the access device 1. The hemostatic valve unit 2 may be pre-mounted on the tube 410 and positioned at the access device 1 by sliding along the tube 410. Alternatively, the hemostatic valve unit 2 may be pre-mounted and releasably attached on the access device 1 and positioned in the transapical passage by sliding along the tube towards the apical puncture hole as described above.

The tube 410 of the applicator tool may then be retracted. It is withdrawn out of the access device and valve that remain in place at the heart, as shown in FIG. 6.

A medical procedure and/or delivery of medical devices may be performed through the port of the valve 2 and the port 120. The method may include for example transapically passing a driving rod 610 of a cardiac assist system into the heart through the hemostatic valve 2 and access device 1.

Delivering medical devices to the heart chamber may include deploying an annuloplasty chain ring at a cardiac valve annulus. A delivery catheter of a delivery system may be introduced for this purpose through the access device 1 with affixed valve 2. The delivery catheter may then be removed out of the patient. Blood leakage from the heart is continued prevented by the hemostatic valve unit 2.

A sealing device may be slid over the driving rod 610 through the valve 2 and affixed at the access device 1 providing a sealed access device 1 with a wet/dry zone separation. The proximal end of the driving rod 610 may then be connected to a drive unit 6 while attaching the drive unit 6 to the access device 1.

The sealing device 3 may be introduced through the hemostatic valve unit 2 to the access device 1 sealing the transapical passage, e.g. as described above for creating the wet/dry zone separation. An element like a rod may pass across the through port of the sealing element 3. Alternatively, the distal end port of sealing unit 3 may be provided as a closed element like a membrane or hub. A magnetic coupling 340 to an element in the heart chamber may be established with units shown in FIGS. 24A, 24B and 24C.

The valve 2 may then be removed as well as a medical device affixed to the access device prior to concluding the procedure. The method 700 may include removing the hemostatic valve unit from the apical base plate by disconnecting the hemostatic valve unit from the apical base plate and withdrawing the hemostatic valve unit out of the patient, or splitting or partitioning the hemostatic valve unit.

In addition, examples of the disclosure may include one or more sensors. For instance, the access device 1, the hemostatic valve 2, the sealing unit 3, the drive unit for cardiac assist 6, the transapical access system 5, or other medical devices (not shown) attachable to the access device 1 may include such sensor(s) thus implantable into a patient's body.

Sensors often need to be part of a wet zone and a dry zone, since measurement is often performed in blood (wet zone) and sensors often include electrical parts that need to be separated from blood in a dry zone. Thus, it is important to have a feed-through port 320 in order to facilitate this sensor wet and dry zone separation.

Hence, some examples of the disclosure include in addition one or multiple optional sensors 620.

Such sensor may go through the feed-through port 320 of the bellows 310, instead of the driving rod 610 as previously described. In another alternative/example, there may be more than one (multiple) feed-through ports 320 so that multiple sensors and/or the driving rod 610 could go through different feed-through ports 320 at the same time. The feed-through port 320 does not need to be part of the bellows 310, as previous described, but may be a separate part/unit of the sealing unit 3 instead. An example of a multiple feed-through, or multi-lumen, ports 320 is for instance including a preferably separate channel for a sensor, such as a pressure sensor, (not shown in the Figures).

In one example, the sensor 620 may include one or more pressure sensors e.g. connectable to a port distally ending in the chamber of the heart. This will provide intracardiac pressure of e.g. the left and/or right ventricle of the heart. The pressure data not only provides important clinical data but may also be used in control algorithms of an implanted medical device. Other relevant clinical parameters, e.g. the heart rate of the patient and/or various heart arrhythmias, may also be extracted from the pressure data.

In one example, the sensor 620 may include additionally, or alternatively, one or more ECG electrodes e.g. connectable to a port distally ending in the heart. This will provide intracardiac electrical activity of the heart. The ECG data not only provides important clinical data but may also be used in control algorithms of an implanted medical device. Other relevant clinical parameters, e.g. the heart rate of the patient and/or various heart arrhythmias, may also be extracted from the ECG data.

In one example, the sensor 620 may include additionally, or alternatively, one or more optical and/or electrical sensors used for obtaining blood flow and/or blood volume measurements in the heart. Such sensors may e.g. be placed in an optical port and/or window (not shown) facing towards the wet zone of the heart. This may e.g. provide measurement data for intracardiac blood volume of the left ventricle of the heart. The blood flow/volume data not only provides important clinical data but may also be used in control algorithms of an implanted medical device. Other relevant clinical parameters, e.g. the heart rate of the patient and/or stroke volume and/or cardiac output and/or SpO2, may also be extracted from the blood flow/volume data.

In one example, the sensor 620 may include in addition, or alternatively, one or more movement sensors e.g. connectable to a port distally ending in the heart and/or connected to the driving rod 610. This will provide measurement data for intracardiac movement and/or activity data of the heart. The movement data may e.g. represent the up and down movement of the mitral valve and/or the atria/ventricle plane. The movement data not only provides important diagnostic clinical data but may also be used in control algorithms of an implanted medical device. Other relevant clinical parameters, e.g. the heart rate of the patient and/or various heart arrhythmias, may also be extracted from the movement data. Examples of movement sensors include magnetic based, such as a Hall effect sensor, and/or optical based. Examples of movement sensors may also include one or more accelerometers.

The measurement data obtained from the sensor(s) 620 may for instance be used to control a medical device, e.g. be part of a control algorithm implemented in the hardware and/or software of the medical device such as a cardiac assist system. The data from the sensors may for instance also be used to monitor important physiological properties and/or use the sensor data to extract and/or calculate critical clinical parameters that need to be monitored. Besides from monitoring the physiological properties and/or clinical parameters, they may be part of a surveillance system. Obtaining and managing patient data is not only important for e.g. the safety of the patient and the functionality of a medical device, but also due to regulatory requirements for medical devices since it will be mandatory to collect, retain, and analyze post-market clinical data.

Such measurement data, providable by sensors 620, when implanted with examples of devices described herein, has hitherto been difficult to provide.

FIG. 27 illustrates steps of an example of a method 800 of transapically implanting a cardiac assist system. The method 800 or medical procedure includes attaching 810 a cardiac assist unit 6 to an access device 1 including a sealed apical base plate 100. The apical base plate 100 has a sealed tubular through port arranged across cardiac tissue to a heart chamber. A flange unit is attached to the base plate 100 and to the heart 10. The access device 1 has a sealing unit 3 attached thereto. The method may include inserting a delivery tube through a hemostatic valve attached to the access device prior to sealing the access device for providing a wet/dry zone as described above.

Some additional examples of the disclosure are given below.

Example 31. An applicator tool (4) for creating a transapical passage on a beating heart, said applicator tool (4) including

- a harpoon (450) insertable through a tube (410) and having a distal tip configured to penetrate cardiac tissue at an apex of said heart; and
- said tube (410) having a sharpened edge at a distal end configured to cut said cardiac tissue at said apex to a transapical hole in said heart, and said harpoon having an expandable flange for preventing withdrawal of said harpoon through said cardiac tissue, wherein said flange is configured to keep said cut cardiac tissue within said tube (410).

32. The applicator tool of example 31, wherein said distal end of said tube is in fluid communication with a proximal seal including a blood indicator (490).

33. The applicator tool of example 31 or 32, wherein said distal end of said tube (410) is configured for apposition to said cardiac tissue at said apex.

34. The applicator tool of any of examples 31 to 33, comprising

- an access device (1) for a heart having a tubular through port (120) adapted to be arranged across said cardiac tissue when advanced over said tube (410).

35. The applicator tool of example 34, wherein a removable hemostatic valve unit (2) is attachable to said access device (1) and slidable over said tube (410).

36. The applicator tool of any of examples 31 to 35, in combination comprising a dilator having a larger diameter than said transapical hole in use made in said heart by said tube (410) and said dilator being configured to widen said transapical hole when inserted therein.

Example 37. An applicator tool (4) for creating a transapical passage on a beating heart, said applicator tool (4) including

- a penetration needle (460) insertable through a co-axial dilator (480) having a distal tip configured to penetrate cardiac tissue at an apex to provide an opening, and said dilator (480) to widen said opening of said cardiac tissue; and
- an access device (1) for a heart having a tubular through port (120) adapted to be arranged across said cardiac tissue when advanced over said dilator (480), and/or wherein said distal end of said penetration needle is in fluid communication with a proximal seal including a blood indicator.

38. The applicator tool of example 37, wherein a removable hemostatic valve unit (2) is attachable to said access device (1) and slidable over said dilator (480).

Example 39. A transapical access system for creating a transapical passage on a beating heart, said system including an access device (1) for a heart according to any of originally filed PCT claims 1 to 21, and/or

- an applicator tool (4) for creating a transapical passage and delivering said access device (1) to an apex of said heart according to any of examples 31 to 38.

40. The system of example 39, comprising a fixture template (190) for targeted puncture of said apex.

41. The system of example 40, wherein said fixture (190) has a patient specific shape for said apex, such as selected from multiple fixtures or manufactured based on imaging data of said apex.

Example 42. A method of creating a transapical passage on a beating heart, said method including

- determining a position on an apex region for creating a transapical passage
- creating a transapical hole at said determined apex region through cardiac muscle tissue,
- delivering an access device having a through port to said transapical hole,
- attaching a flange unit of said access device to said heart, and
- removably connecting a hemostatic valve unit to said access device.

43. The method of example 42, including arranging a plurality of sutures at said transapical hole for said attaching said flange unit of said access device to said heart.

44. The method of any of examples 42 to 43, including cutting said cardiac tissue at said apex with a sharpened edge at a distal end of a tube.

45. The method of any of examples 42 to 44, including preventing withdrawal of a harpoon through said cardiac tissue by expanding a flange of said harpoon.

46. The method of any of examples 42 or 43, including creating said transapical hole with an applicator tool including penetrating cardiac tissue at said apex with a distal tip of a harpoon member through a tube.

47. The method of any of examples 45 or 46, including keeping said cut cardiac tissue within said tube by said expanded flange of said harpoon member.

48. The method of any of examples 42 to 47, including indicating penetration of said cardiac tissue into an interior of said heart with a blood indicator at distal end of a tube of an applicator tool being in fluid communication with a proximal seal including a blood indicator.

49. The method of example 42 or 43, including creating said transapical passage with an applicator tool including penetrating cardiac tissue at an apex with a penetration needle of said applicator tool insertable through a co-axial dilator having a distal tip dilating said cardiac tissue.

50. The method of example 49, including arranging a tubular through port of said access device across said cardiac tissue when advanced over said dilator.

51. The method of example 50, including removably attaching a removable hemostatic valve unit to said access device and sliding said removable hemostatic valve unit over said dilator.

52. The method of any of examples 42 to 51, including

- transapically passing a driving rod of a cardiac assist unit into said heart through said hemostatic valve;
- attaching a sealing unit to said access device through said hemostatic valve unit and over said driving rod;
- sealing said transapical passage through said access device by said sealing unit;
- removing said hemostatic valve unit from said access device;

53. The method of example 52 including said

- removing said hemostatic valve unit from said access device by
- disconnecting said hemostatic valve unit from said access device and withdrawing said hemostatic valve unit out of the patient, or
- splitting or partitioning said hemostatic valve unit.

54. The method of any of examples 42 to 53, including deploying an annuloplasty chain ring at a cardiac valve annulus.

55. The method of any of examples 42 to 54, including removing a delivery tube out of patient and sealing against blood leakage from said heart by a hemostatic valve unit.

56. The method of any of examples 42 to 54, wherein said applicator tool is the applicator tool of any of examples 22 to 29, said access device is the access device of any of originally filed PCT claims 1 to 21, and/or said hemostatic valve is that of any of originally filed PCT claims 22 to 26.

Example 57. A method of transapically implanting a medical device on a beating heart including

- removably attaching said medical device to a sealed access device (1) affixed to said heart.

58. The method of example 57, said access device having a sealed tubular through port adapted to be arranged across cardiac tissue to a heart chamber,

- and a flange unit sealingly affixing said access device to said heart.

59. The method of any of examples 57 to 58, including attaching a sealing unit to said access device for creating a separation of a wet zone and a dry zone inside a mammal body.

60. The method of any of examples 57 to 59, including inserting a delivery tube through a hemostatic valve attached to said access device.

61. The method of any of examples 57 to 60, including attaching said medical device to said sealed access device while a hemostatic valve and a sealing unit are attached to said access device, and detaching said hemostatic valve by splitting or peeling-off said hemostatic valve.

62. The method of any of examples 57 to 61, wherein said medical device is removably attached to said sealed access device.

63. The method of any of examples 57 to 62, wherein said medical device is comprised in a cardiac assist system.

64. The method of any of examples 57 to 63, wherein said access device is the access device of any of originally filed PCT claims 1 to 21, and/or said hemostatic valve is that of any of originally filed PCT claims 21 to 26.

65. A method of accessing a heart of a patient comprising:
accessing said heart of said patient;
accessing a heart chamber of said heart;
securing a base plate at an apex region of said heart and extending to said heart chamber;
associating a sealing unit with said base plate and thereby creating a dry zone isolated from said heart chamber;

It should be noted that the skilled person will understand that some of the devices disclosed herein in combination with other devices can be provided and implemented as standalone devices, independent of the other devices or combined systems and methods described herein. An example is the access device 1, which can be provided as an access port to the inner of the heart for other applications than described herein. Another example is the application tool 4 that may be provided to safely puncture a tissue wall and provide the tissue wall with a tissue passage. Also, the removable hemostatic valve 2 may be provided for attachment to other units than an access device 1.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention has been described above with reference to specific embodiments. However, other embodiments than the above described are equally possible within the scope of the invention, which is only limited by the appended patent claims.

LIST OF REFERENCE SIGNS

- 1 access device for a heart
  - 100 apical base plate
  - 110 connection interface
  - 115 locking unit
  - 120 tubular through port
  - 125 sealing surface for sealing unit 3
  - 130 sealing surface for hemostatic valve 2
  - 150, 151 mounting spikes
  - 155 bayonet joint
  - 160 flange unit
  - 165 sutures
  - 170 suture hole
  - 190 template for positioning an access device
  - 191 cut-outs of template
  - 192 cut-outs for suture stitching
- 2 hemostatic valve unit (inflatable valve assembly)
  - 200 housing
  - 202, 204 splittable housing parts
  - 210 inflation port
  - 220 inflatable balloon member
  - 222 balloon lobe
  - 225 valve through port
  - 230 sealing surface for sealing against access device 1
  - 250, 251 Mounting apertures (mating with 150,151)
  - 255 bayonet pins for joint 155
  - 260 sealing element
- 3 sealing unit (bellows assembly)
  - 310 bellows
  - 320 feed-through port
  - 325 first sealing member for sealing against access device
  - 326 second sealing member for sealing feed through port
  - 330 detaining unit
  - 340 magnetic coupling
- 4 applicator tool for creating a transapical passage (apex punch assembly)
  - 400 pistol grip
  - 410 tube
  - 412 sharp tip of tube
  - 415 trigger for pushing tube 410 forward
  - 417 claw
  - 420 control dial for rotating tube
  - 450 harpoon
  - 455 proximal end of harpoon 450/rod 470
  - 460 penetration needle
  - 461 seat
  - 465 needle trigger
  - 466 needle spring
  - 467 safety pin
  - 470 rod
  - 471 shoulder
  - 472 head (distal end portion) of rod with retaining unit
  - 473 retaining unit e.g. barb, hook or fluke or wire mesh
  - 474 moveable and lockable stop element
  - 475 tissue plug
  - 480 dilator
  - 490 penetration/blood indicator
- 5 transapical access system
- 6 drive unit for cardiac assist
  - 610 driving rod
  - 620 sensor
  - 630 electrical connection
  - 650 anchor unit/annuloplasty implant
- 7 delivery system
  - 70 delivery tube
  - 72 inserter unit
  - 74 pusher
- 700 a method of creating a transapical passage on a beating heart
  - 710-730 method steps
- 800 a method of transapically implanting a cardiac assist system
  - 810 method step
- 10 heart
  - 12 apex region of heart 10
  - 14 outside of heart
  - 15 inside of heart
  - 20 heart chamber
  - 30 Wet zone
  - 32 Dry zone

What is claimed is:

1. A device for accessing an interior of a heart comprising:
an implantable apical base plate;
a connection interface associated with the apical base plate;
the device connectable to a removable hemostatic valve and a cardiac assist device in each of the following configurations:

a first sealed configuration wherein the connection interface is coupled only with the removable hemostatic valve;

a second sealed configuration wherein the connection interface is coupled with both the removable hemostatic valve and the cardiac assist device; and, a third sealed configuration wherein the connection interface is coupled only with the cardiac assist device.

2. The device of claim 1, wherein said connection interface includes a connection hole.

3. The device of claim 2 further comprising a screw configured to secure a medical device through said connection hole.

4. The device of claim 1, wherein said connection interface comprises a locking unit for securing the coupling of the cardiac assist device.

5. A device for accessing an interior of a heart comprising:

a permanently implantable apical base plate;

a connection interface associated with the apical base plate;

the device connectable to a removable hemostatic valve and a cardiac assist device in each of the following configurations;

a first sealed configuration wherein the connection interface is engaged only with the removable hemostatic valve;

a second sealed configuration wherein the connection interface is engaged with both the removable hemostatic valve and with the cardiac assist device; and, a third sealed configuration wherein the connection interface is engaged only with the cardiac assist device.

6. The device of claim 5, wherein said connection interface includes a connection hole.

7. The device of claim 6 further comprising a screw configured to secure a medical device through said connection hole.

8. The device of claim 5, wherein the connection interface is removable from the apical base plate.

9. A device for accessing an interior of a heart comprising:

a permanently implantable base plate;

a connection interface attached to the apical base plate;

the device connectable to a removable hemostatic valve and a cardiac assist device in each of the following configurations;

a first sealed configuration wherein the connection interface is connected with the removable hemostatic valve;

a second sealed configuration wherein the connection interface is connected with both the removable hemostatic valve and the cardiac assist device; and, a third sealed configuration wherein the connection interface is connected only with the cardiac assist device.

10. The device of claim 9, wherein said connection interface includes a connection hole.

11. The device of claim 10, further comprising a screw configured to secure a medical device through said connection hole.

12. The device of claim 9, wherein the connection interface is removably associated with the base plate.

13. The device of claim 9, wherein said connection interface comprises a locking unit for securing the connection of the cardiac assist device.

* * * * *